United States Patent [19]

Jansz et al.

[11] Patent Number: 4,720,483
[45] Date of Patent: Jan. 19, 1988

[54] OLIGOPEPTIDES AND INTERMEDIATES AND PROCESSES FOR THEIR MANUFACTURE

[75] Inventors: Hendrik S. Jansz, Zeist; Cornelis J. M. Lips, The Hague; Paul H. Steenbergh, Bunnik, all of Netherlands; Hans Rink, Riehen; Peter Sieber, Reinach, both of Switzerland

[73] Assignee: Ciba-Geigy Corporation, Ardsley, N.Y.

[21] Appl. No.: 819,168

[22] Filed: Jan. 15, 1986

[30] Foreign Application Priority Data

Jan. 16, 1985 [CH] Switzerland ............... 188/85

[51] Int. Cl.$^4$ .................. A61K 37/24; C07K 7/10
[52] U.S. Cl. ........................ 514/11; 514/12; 530/324; 530/307
[58] Field of Search ............ 514/11, 12; 530/324, 530/307

[56] References Cited

U.S. PATENT DOCUMENTS 4,530,838 7/1985 Evans et al. .............. 514/11
4,549,986 10/1985 Evans et al. .............. 530/324

FOREIGN PATENT DOCUMENTS

WO85/43    1/1985  PCT Int'l Appl.
WO85/1658  4/1985  PCT Int'l Appl.

OTHER PUBLICATIONS

The Merck Index, 10th Ed., pp. 515–516.
Steenberg, FEBS Letter 183: 403–407 (1985).
Hoppener, Human Genetics 70: 259–263 (1985).
Morris, Nature 308: 746–748 (1984).
Brain, Nature 313, pp. 54–56 (1985).

Primary Examiner—Delbert R. Phillips
Attorney, Agent, or Firm—Michael W. Glynn; Irving M. Fishman

[57] ABSTRACT

Described are peptides that have, as partial sequence of a larger peptide, or exclusively, the amino acid sequence of the formula I (I)

—AlaCysAsnThrAlaThrCysValThrHisArgLeuAlaGlyLeuLeuSer—

ArgSerGlyGlyMetValLysSerAsnPheValProThrAsnValGlySer—

LysAlaPhe— in which the cysteine residues can form intra- or intermolecular disulphide bridges, and derivatives thereof having an amidated terminal carboxy group and/or an acylated terminal amino group, and their salts, DNA sequences that code for the mentioned peptides, microorganisms that contain these DNA sequences, processes for the manufacture thereof, pharmaceutical preparations that contain the mentioned peptides in the form of their amides, and the use of these peptide-amides for the treatment of coronary circulation disorders and bone metabolism disorders.

9 Claims, No Drawings

OLIGOPEPTIDES AND INTERMEDIATES AND PROCESSES FOR THEIR MANUFACTURE

The invention relates to novel peptides of which the structure is derived from the human calcitonin gene, that is to say so-called "calcitonin gene related peptides (CGRP)", and salts thereof, to corresponding DNA sequences and microorganisms that contain these DNA sequences and that are capable of producing the peptides according to the invention as intermediates for the manufacture of these peptides, to processes for the manufacture of the peptides or DNA sequences, to pharmaceutical preparations that contain the said peptides or salts thereof, and to the use of these peptides or salts thereof as medicaments.

Thus, the invention relates first especially to peptides that have, as a partial sequence of a larger peptide, or exclusively, the amino acid sequence of the formula I —AlaCysAsnThrAlaThrCysValThrHisArgLeuAlaGlyLeuLeuSer— (I)

ArgSerGlyGlyMetValLysSerAsnPheValProThrAsnValGlySer—

LysAlaPhe— which the cysteine residues can form intra- or intermolecualr disulphide bridges, and to derivatives thereof having an amidated terminal carboxy group and/or an acylated terminal amino group, and to their salts.

The above-mentioned larger peptide has especially up to 90, above all up to 80, for example, up to 72, amino acid residues. Preferably it has the amino acid sequence of the formula II —AspTyrValGlnMetLysAlaSerGluLeuLysGlnGluGlnGluThrGlnSer— (II)

SerSerSerAlaAlaGlnLysArgAlaCysAsnThrAlaThrCysValThrHisArg—

LeuAlaGlyLeuLeuSerArgSerGlyGlyMetValLysSerAsnPheValProThr—

AsnValGlySerLysAlaPheGlyArgArgArgSerAspLeuGluAla— or a fragment thereof, that has, in addition to at least one additional amino acid residue, the sequence of the formula I.

Preferably, the two cysteine residues form an intramolecular disulphide bridge with each other. It is, however, also possible, for example, for dimers to be formed, the two peptide chains being linked to one another head to head or, preferably, head to tail, that is, in antiparallel, via intermolecular disulphide bridges.

The terminal amino group is preferably free, but can also be acylated, such as, especially, acetylated.

Those of the above-mentioned peptides in which the terminal carboxy group is in amidated form, that is to say, especially in the form of a carbamoyl group, are pharmacologically active. The above-mentioned peptides in which the terminal carboxy group is in free or in salt form also form part of the invention as intermediates for the manufacture of pharmacologically active amides.

The invention relates first and foremost to the peptide-amide of the formula III $$\text{Ala}\overset{S\rule{2cm}{0.4pt}S}{-\underset{|}{\text{Cy}}-\text{Asn}-\text{Thr}-\text{Ala}-\text{Thr}-\underset{|}{\text{Cy}}-\text{Val}-\text{Thr}-\text{His}-} \quad (III)$$

—Arg—Leu—Ala—Gly—Leu—Leu—Ser—Arg—Ser—

—Gly—Gly—Met—Val—Lys—Ser—Asn—Val—

—Pro—Thr—Asn—Val—Gly—Ser—Lys—Ala—Phe—NH$_2$ (CGRP II) and salts thereof.

In addition, the invention relates also to the N-acetylated peptide-amide of the formula IIIa $$CH_3-\overset{O}{\underset{\|}{C}}-\text{Ala}-\overset{S\rule{2cm}{0.4pt}S}{\underset{|}{\text{Cy}}-\text{Asn}-\text{Thr}-\text{Ala}-\text{Thr}-\underset{|}{\text{Cy}}-\text{Val}-\text{Thr}-} \quad (IIIa)$$

—His—Arg—Leu—Ala—Gly—Leu—Leu—Ser—Arg—Ser—

—Gly—Gly—Met—Val—Lys—Ser—Asn—Phe—Val—

—Pro—Thr—Asn—Val—Gly—Ser—Lys—Ala—Phe—NH$_2$.

The invention relates also to peptides of the formula IIIb $$\text{Ala}-\overset{S\rule{2cm}{0.4pt}S}{\underset{|}{\text{Cy}}-\text{Asn}-\text{Thr}-\text{Ala}-\text{Thr}-\underset{|}{\text{Cy}}-\text{Val}-\text{Thr}-\text{His}-} \quad (IIIb)$$

—Arg—Leu—Ala—Gly—Leu—Leu—Ser—Arg—Ser—

—Gly—Gly—Met—Val—Lys—Ser—Asn—Phe—Val—

—Pro—Thr—Asn—Val—Gly—Ser—Lys—

—Ala—Phe—AS$^\Omega$—OH in which AS$^\Omega$ represents an amino acid such as, preferably, glycine or tyrosine, which can be degraded enzymatically to the NH$_2$ group of the terminal amide group of the peptide-amide of the formula III or can be substituted by ammonia in the presence of a suitable enzyme, and to derivatives thereof in which the terminal amino group is acetylated.

In agreement with the internationally recognised nomenclature rules, the abbreviations for amino acids in this Application, for example the above-mentioned abbreviations, indicate the free acid and, unless stated otherwise, the L-configuration. The α-amino group is to be considered to be at the left-hand side of the abbreviation, the carboxy group at the right-hand side. The absence of an H atom in the α-amino group is marked by a hyphen positioned to the left of the abbreviation for the amino acid. The absence of an HO group in the carboxy group is expressed by a hyphen positioned to the right. Substituents in the side chain of amino acids are placed in brackets directly after the amino acid symbol or are joined to the amino acid symbol by a line passing vertically upwards or downwards therefrom.

The abbreviation

represents cystine.

As yet it is not known whether the peptides according to the invention occur naturally as such, that is to say, for example, in the human organism. Should this, however, be the case, then the invention relates especially to the above-mentioned peptides and salts thereof in a higher concentration than may occur naturally or in extracts that may be known. In particular, the invention relates to the above-mentioned peptides in isolated or purified form, in pure or substantially pure form, in a substantially different surrounding, that is to say with other admixtures, for example admixed pharmaceutical carriers, than those which may occur naturally, in a form suitable for pharmaceutical use, in characterised form and/or in a form outside of a living or dead organism, of an organ, of a cell, of a tissue or of a body fluid. The invention relates especially to the synthetically or genetically produced peptides and their salts.

In the above connection, the term "isolated" means separated from other substances, especially from other chemical compounds, with which the compounds according to the invention may occur naturally. The term "purified" means subjected to chemical and/or physical purification methods. The expression "substantially pure" means a purity of more than 50%.

The invention relates also to the salts, especially the pharmaceutically acceptable non-toxic salts, of the peptides according to the invention. The above-mentioned peptides can form acid addition salts, for example with inorganic acids, especially mineral acids, for example hydrochloric acid, sulphuric acid or phosphoric acid, or salts with organic carboxylic, sulphonic or sulpho acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also amino acids, as well as methanesulphonic acid, ethanesulponic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid.

Those of the above-mentioned peptides which have at least one carboxy group and at least one basic group, for example an amino group, can form internal salts.

Those of the above-mentioned peptides which contain at least one free carboxy group can, especially if they have more carboxy groups than basic groups, form metal or ammonium salts, such as alkali metal and alkaline earth metal salts, for example sodium, potassium, magnesium or calcium salts, as well as ammonium salts with ammonia or suitable organic amines, there coming into consideration for the salt formation especially aliphatic, cycloaliphatic, cycloaliphatic-aliphatic or araliphatic primary, secondary or tertiary mono-, di- or poly-amines, and also heterocyclic bases, such as lower alkylamines, for example triethylamine, hydroxy-lower alkylamines, for example 2-hydroxyethylamine, bis-(2-hydroxyethyl)-amine, 2-hydroxyethyldiethylamine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for examole N,N'-dibenzylethylenediamine, also bases of the pyridine type, for example pyridine, collidine or quinoline.

For isolation or purification it is also possible to use pharmaceutically unsuitable salts. Only the pharmaceutically acceptable non-toxic salts, however, are employed for therapeutic use, and these are therefore preferred.

In femtomol dosages, the peptide-amides according to the invention have a vasodilatory action and result in a reduction of the blood pressure and an increase in the heart rate and in the contractility of the myocardium. The actions are not affected by blockers of the sympathetic nervous system, for example metoprolol [1-isopropylamino-3-(4-{2-methoxyethyl}phenoxy)-propan-2-ol] and Trandate ® (labetalol hydrochloride), whereas the action of noradrenalin and of adrenalin in serum is suppressed by those substances.

Bolus injections of approximately from 100 to 10000 ng of the peptide-amides according to the invention, for example of CGRP II, induce vasodilation, as a function of the concentration, in the isolated perfused mesenteric layer of rats which has been pre-astringed by the infusion of 4 µg/ml of noradrenalin, the vasodilation manifesting itself in a reduction of the perfusion pressure of up to approximately 5300 Pas (40 mm Hg).

In the despinalised rat (Gillesbie and Muir, Brit. J. Pharmacol. 30, 88-98 [1967]), at a dosage of 1 µg/kg/min. the oeptide-amides according to the invention, for example CGRP II, reduce the blood pressure, increase the heart rate by approximately 40 beats per minute and inhibit the pressor effects caused by electro-stimulation of the sympathetic nervous system and by intravenous injection of angiotensin II or adrenalin.

The peptide-amides according to the invention suppress the secretion of gastric juice (secretion volume, release of acid and pepsin) both basally and also after stimulation by bethanechol or histamine. They also act on the central nervous system.

The peptide-amides also have hypocalcaemic activity, that is to say, they reduce the calcium content of the blood and protect the bones from mineral loss.

Owing to the described pharmacological activities, the peptide-amides according to the invention can be used as medicaments, especially for dilating the blood vessels and increasing tissue blood flow, as well as against *Angina pectoris,* hypertension, cardiac insufficiency or other coronary circulation diseases and, in addition, can be used for the same indications as human calcitonin, for example commercially available Cibacalcin ®, for example for bone metabolism disorders, such as osteoporosis or Paget's disease.

The dosage is approximately from 0.1 to 50 ug/kg, preferably approximately from 1 to 10 µg/kg, body weight.

The doses to be administered to a warm-blooded animal, especially man, weighing approximately 70 kg, are from approximately 1 µg to approximately 1000 µg, preferably from approximately 10 µg to approximately 100 µg, for example approximately 40 µg, per day. Administration is preferably parenteral, for example intravenous, on five days of the week for 3 months.

The compounds according to the invention can be manufactured in a manner known per se.

The process according to the invention for the manufacture of the above-mentioned peptides, peptideamides or their derivatives having an acylated terminal amino group is characterised in that (a) an amide bond present in such a compound is formed by reaction of a fragment of this compound that has a free carboxy group, or of a reactive carboxylic acid derivative thereof, with the complementary fragment that has a free amino group, or with a reactive derivative thereof, wherein free functional groups in the mentioned fragments, with the exception of the two groups participating in the reaction, are, if necessary, in protected form, and protecting groups which may be present are removed, or (b) for the manufacture of one of the above-mentioned compounds that has an intra- or inter-molecular disulphide bridge, one of the above-mentioned compounds in which the mercapto groups of the cysteine residues are in free form, or in which the mercapto groups of the cysteine residues are protected by protecting groups that are removed under the reaction conditions, is oxidised with a suitable oxidising agent, or (c) in such a peptide-amide or N-acylated derivative thereof in which at least one functional group is in protected form, the protecting groups present are removed, or (d) for the manufacture of the above-mentioned peptides, host cells transformed with an expression vector containing a DNA sequence that codes for the desired amino acid sequence and that is regulated by an expression control sequence are cultivated in a liquid nutrient medium containing assimilable carbon and nitrogen sources, the product is, if necessary, freed from the host cells and isolated and, if necessary, a dimer or polymer which may be obtained is reacted with a reducing agent suitable for splitting disulphide bonds and, if necessary, the resulting reduced product is treated with an oxidising agent suitable for the new linking of disulohide bonds, or (e) for the manufacture of one of the above-mentioned peptide-amides, a peptide that in addition to the amino acid sequence of the desired peptide-amide has C-terminally an amino acid $AS^\Omega$ that can be degraded enzymatically to the $NH_2$ group of the terminal amide group of the desired peptide-amide or that can be substituted by ammonia in the presence of a suitable enzyme, is treated by means of a suitable enzyme optionally in the presence of ammonia, and, if desired, after carrying out one of the process variants (a-e), a resulting salt is converted into the free compound or a resulting free compound is converted into a salt.

The above-mentioned process variants are explained in detail in the following:

Process a

According to this process, as the last stage of the reaction in the synthesis of the end product an amide bond is formed at any position of the molecule. The mentioned fragment that has a free carboxy group may be either a single amino acid or a di-, oligo- or poly-peptide or, in the case of the derivatives having an acylated terminal amino group, the acylating carboxylic acid, such as, especially, acetic acid. The above-mentioned fragment that has a free amino group is a single amino acid, a di-, oligo- or polypeptide or, when producing peptide-amides, also an amine, such as, especially, ammonia.

Preferably, the reaction is carried out by reacting a reactive carboxylic acid derivative of the one fragment with the complementary fragment that has a free amino group, it being possible for the activation of the carboxyl group of the carboxylic acid derivative to be effected in situ.

Reactive carboxylic acid derivatives are especially reactive activated esters or reactive anhydrides, also reactive cyclic amides; reactive acid derivatives can also be formed in situ.

Activated esters of acids are especially esters that are unsaturated at the linking carbon atom of the esterifying radical, for example of the vinyl ester type, such as true vinyl esters (which can be obtained, for example, by the transesterification of a corresponding ester with vinyl acetate, activated vinyl ester method), carbamoylvinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-disubstituted amidino esters (which can be obtained, for example, by treating the corresponding acid with a suitable N,N'-disubstituted carbodiimide, for example N,N'-dicyclohexylcarbodiimide; carbodiimide method), or N,N-disubstituted amidino esters (which can be obtained, for example, by treating the corresponding acid with an N,N-disubstituted cyanamide; cyanamide method), suitable aryl esters, especially phenyl esters suitably substituted by electron-attracting substituents (which can be obtained, for example, by treating the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (which can be obtained, for example, by treating the corresponding acid with chloroacetonitrile in the presence of a base; cyanomethyl esters method), thioesters, especially phenylthio esters optionally substituted, for example, by nitro (which can be obtained, for example, by treating the corresponding acid with a thiophenol optionally substituted, for example, by nitro, inter alia with the aid of the anhydride or carbodiimide method; activated thiol esters method), amino or amido esters (which can be obtained, for example, by treating the corresponding acid with an N-hydroxyamino or N-hydroxyamido compound, for example N-hydroxysuccinimide, N-hydroxypiperidine, N-hydroxyphthalimide or 1-hydroxybenzotriazole, for example according to the anhydride or carbodiimide method; activated N-hydroxy esters method) or silyl esters (which can be obtained, for example, by treating the corresponding acid with a silylating agent, for example hexamethyl disilazane, and which readily react with hydroxy groups but not with amino groups).

Acid anhydrides may be symmetrical or preferably mixed anhydrides of these acids, for example anhydrides with inorganic acids, such as acid halides, especially acid chlorides (which can be obtained, for example, by treating the corresponding acid with thionyl chloride, phosphorus pentachloride or oxalyl chloride; acid chloride method); azides (which can be obtained, for example, from a corresponding acid ester by way of the corresponding hydrazide and treatment thereof with nitrous acid; azide method), anhydrides with carbonic acid semi-derivatives, such as with corresponding esters, for example carbonic acid lower alkyl semiesters (which can be obtained, for example, by treating the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed 0-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an optionally substituted lower alkanecarboxylic or phenylalkanecarboxylic acid halide, for example phenylacetic acid, pivalic acid or trifluoroacetic acid chloride; mixed carboxylic acid anhydrides method) or with organic sulphonic acids (which can be obtained, for example, by treating a salt, such as an alkali metal salt, of the corresponding acid with a suitable organic sulphonic acid halide, such as lower alkanesulphonic or arylsulphonic acid chloride, for example methane- or p-toluene-sulphonic acid chloride; mixed sulphonic acid anhydrides method), as well as symmetrical anhydrides (which can be obtained, for example, by condensation of the corresponding acid in the presence of a carbodiimide or of 1-diethylaminopropyne; symmetrical anhydrides method).

Suitable cyclic amides are especially amides with five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5dimethylpyrazole (which can be obtained, for example, by way of the acid hydrazide by treatment with acetylacetone; pyrazolide method).

As mentioned, the carboxylic acid derivatives can also be formed in situ. For example, N,N'-disubstituted amidino esters can be formed in situ by reacting a mixture of the complementary fragment having the free amino group and the peptide fragment having a free carboxy group in the presence of a suitable N,N-disubstituted carbodiimide, for example N,N'-dicyclohexylcarbodiimide. Further, amino or amido esters of the acid can be formed in the presence of the amine to be acylated by reacting a mixture of the corresponding acid and amino starting materials in the presence of an N,N'-disubstituted carbodiimide, for example N,N'-dicyclohexylcarbodiimide, and in the presence of an N-hydroxyamine or N-hydroxyamide, for example N-hydroxysuccinimide, optionally in the presence of a suitable base, for example 4-dimethylaminopyridine.

Alternatively, process variant (a) can also be carried out by reacting a fragment having a free carboxy group with the complementary fragment in which the amino acid is present in reactive form. The amino group can be activated, for example, by reaction with a phosphite, for example diethyl chlorophosphite, 1,1-phenylene chlorophosphite, ethyl dichlorophosphite, ethylene chlorophosphite or tetraethyl pyrophosphite.

The amino group can also be activated by bonding to halocarbonyl, for example chlorocarbonyl, or can be activated in the form of an isocyanate group.

Free functional groups in the mentioned fragments which, if they are not to participate in the reaction, are advantageously in protected form, are especially carboxy, amino, hydroxy and mercapto groups.

Protecting groups and the manner in which they are introduced and removed are described, for example, in "Protective Groups in Organic Chemistry", Plenum Press, London, New York 1973, and in "Methoden der organischen Chemie", Houben-Weyl, 4th Edition, Vol. 15/1, Georg-Thieme-Verlag, Stuttgart 1974 and in Theodora W. Greene, "Protective Groups in Organic Synthesis", John Wiley & Sons, New York 1981. It is characteristic of protecting groups that they can be readily removed, that is to say without undesired secondary reactions taking place, for example by solvolysis, reduction, photolysis or alternatively under physiological conditions.

Hydroxy-protecting groups are, for example, acyl radicals, such as optionally substituted, for example halo-substituted, lower alkanoyl, such as 2,2-dichloroacetyl, or acyl radicals of carbonic acid semi-esters, especially tert.-butoxycarbonyl, optionally substituted benzyloxycarbonyl or diphenylmethoxycarbonyl, for example 4-nitrobenzyloxycarbonyl, or 2-halo-lower alkoxycarbonyl, such as 2,2,2-trichloroethoxycarbonyl, also trityl or formyl, or organic silyl or stannyl radicals, also readily removable etherifying groups, such as tert.-lower alkyl, for examole tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also optionally substituted 1-phenyl-lower alkyl, such as optionally substituted benzyl or diphenylmethyl, there being suitable as substituents of the phenyl radicals, for example, halogen, such as chlorine, lower alkoxy, such as methoxy, and/or nitro.

Carboxy groups are customarily protected in esterified form, such ester groupings being readily cleavable under mild conditions. Carboxy groups protected in this manner contain as esterifying groups especially lower alkyl groups that are branched in the 1-position or suitably substituted in the 1- or 2-position. Preferred carboxy groups in esterified form are, inter alia, tert.-lower alkoxycarbonyl, for example tert.-butoxycarbonyl, arylmethoxycarbonyl having one or two aryl radicals, these being phenyl radicals optionally mono- or poly-substituted, for example, by lower alkyl, such as tert.-lower alkyl, for example tert.-butyl, lower alkoxy, such as methoxy, hydroxy, halogen, for example chlorine, and/or by nitro, such as benzyloxycarbonyl optionally substituted, for example, as mentioned above, for example 4-methoxybenzyloxycarbonyl or 4-nitrobenzyloxycarbonyl, or diphenylmethoxycarbonyl optionally substituted, for example, as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group is benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, represents an aliphatic, araliphatic, cycloaliphatic or aromatic hydrocarbon radical that is optionally substituted, for example, by lower alkyl, lower alkoxy, aryl, halogen and/or by nitro, such as corresponding optionally substituted lower alkyl, phenyl-lower alkyl, cycloalkyl or phenyl, for example 2-tri-lower alkylsilylethoxycarbonyl, 2-trimethylsilylethoxycarbonyl or 2-(di-n-butylmethyl-silyl)-ethoxycarbonyl, or 2-triarylsilylethoxycarbonyl, such as 2-triphenylsilylethoxycarbonyl.

The organic silyl or stannyl radicals mentioned hereinbefore and hereinafter preferably contain lower alkyl, especially methyl, as substituent of the silicon or tin atoms. Corresponding silyl or stannyl groups are especially tri-lower alkylsilyl, especially trimethylsilyl, also dimethyl-tert.-butylsilyl, or correspondingly substituted stannyl, for example tri-n-butylstannyl.

Preferred protected carboxy groups are tert.-lower alkoxycarbonyl, such as tert.-butoxycarbonyl, and especially benzyloxycarbonyl or diphenylmethoxycarbonyl optionally substituted, for example, as mentioned above, such as 4-nitrobenzyloxycarbonyl, and more especially 2-(trimethylsilyl)-ethoxycarbonyl, as well as 4-benzyloxycarbonylbenzyloxycarbonyl in which the phenyl group of the first-mentioned benzyloxycarbonyl radical is linked to a polymer carrier, that is, for example, linked to polystyrene, which is crosslinked by divinylbenzene.

A protected amino group can be, for example, in the form of a readily cleavable acylamino, arylmethylamino, etherified mercaptoamino, 2-acyl-lower alk-1-enylamino, silylamino or stannylamino group or in the form of an azido group.

In a corresponding acylamino group, acyl is, for example, the acyl radical of an organic carboxylic acid having, for example, up to 18 carbon atoms, especially an alkanecarboxylic acid optionally substituted, for example, by halogen or aryl, or of benzoic acid optionally substituted, for example, by halogen, lower alkoxy or nitro, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl optionally substituted, for example, by halogen, lower alkoxy or by nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals that are preferably phenyl optionally mono- or polysubstituted, for example, by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4nitrobenzyloxycarbonyl, or substituted diphenylmethoxycarbonyl, for example benzhydryloxycarbonyl or di-(4-methoxyphenyl)-methoxycarbonyl, aroylmethoxycarbonyl in which the aroyl group is preferably benzoyl optionally substituted, for examole, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)ethoxycarbonyl in which each of the substituents, independently of the others, represents an aliphatic, araliphatic, cycloaliphatic or aromatic hydrocarbon radical that has up to 15 carbon atoms and is optionally substituted, for example, by lower alkyl, lower alkoxy, aryl, halogen or by nitro, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethylsilyl)ethoxycarbonyl, or 2-triarylsilylethoxycarbonyl, such as 2-triphenylsilylethoxycarbonyl.

Further acyl radicals coming into consideration as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, di-(phenyl-lower alkyl)-phosphoryl that is optionally substituted, for example, by nitro, for example dibenzylphosphoryl or di-(4-nitrobenzyl)-phosphoryl, optionally substituted phenoxyphenylphosphonyl, for example phenoxyphenylphosphonyl, di-lower alkylphosphinyl, for example diethylphosphinyl, or optionally substituted diphenylphosphinyl, for example diphenylphosphinyl.

In an arylmethylamino group that is a mono-, di- or especially tri-arylmethylamino group, the aryl radicals are especially optionally substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl that is optionally substituted, for example, by lower alkyl, such as methyl or tert.-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that may be used as an amino-protecting group, acyl is, for example, the corresponding radical of a lower alkanecarboxylic acid, of a benzoic acid that is optionally substituted, for example, by lower alkyl, such as methyl or tert.-butyl, lower alkoxy, such as methoxy, halogen, such as chlorine, and/or by nitro, or especially of a carbonic acid semi-ester, such as a carbonic acid lower alkyl semi-ester. Corresponding protecting groups are especially 1-lower alkanoylprop-1-en-2-yl, for example 1-acetyl-prop-1-en-2-yl, or 1-lower alkoxycarbonylprop-1-en-2-yl, for example 1-ethoxy-carbonylprop-1-en-2-yl.

An amino group can also be protected in protonated form; as corresponding anions there come into consideration especially those of strong inorganic acids, such as hydrohalic acids, for example the chlorine or bromine anion, or organic sulphonic acids, such as p-toluenesulphonic acid.

Preferred amino-protecting groups are acyl radicals of carbonic acid semi-esters, especially tert.-butoxycarbonyl, or benzyloxycarbonyl or diphenylmethoxycarbonyl each of which is optionally substituted, for example as indicated, for example 4-nitrobenzyloxycarbonyl, or 2-halo-lower alkoxycarbonyl, such as 2,2,2-trichloroethoxycarbonyl, also trityl or formyl.

A mercapto group, such as, for example, in cysteine, can be protected especially by S-alkylation with optionally substituted alkyl radicals, by thioacetal formation, S-acylation or by establishing asymmetrical disulphide groupings. Preferred mercapto-protecting groups are, for example, benzyl optionally substituted in the phenyl radical, for example by methoxy or nitro, such as 4-methoxybenzyl, diphenylmethyl optionally substituted in the phenyl moiety, for example by methoxy, such as 4,4'-dimethoxydiphenylmethyl, triphenylmethyl, trimethylsilyl, benzylthiomethyl, tetrahydropyranyl, acylaminomethyl, for example acetylaminomethyl, benzoyl, benzyloxycarbonyl or aminocarbonyl, such as ethylaminocarbonyl.

Primary carboxylic acid amide groups (—CONH₂) are protected, for example, in the form of N-(9-xanthenyl) derivatives or in the form of N-(mono-, di- or triarylmethyl) derivatives, aryl being especially unsubstituted phenyl or phenyl substituted by up to 5 identical or different substituents. Such phenyl substituents are preferably lower alkyl, such as methyl, lower alkoxy, such as methoxy, or expressly also polymeric carriers. There may be mentioned as examples of such arylmethyl protecting groups 4-methoxybenzyl, 2,4,6-trimethoxybenzyl, diphenylmethyl, di-(4'-methoxyphenyl)-methyl, di-(4-methylphenyl)-methyl and (4-methylphenyl)-([polymeric carrier]-phenyl)-methyl.

Guanidino grouos are protected, for example, in the form of toluenesulponate.

In this Applicaton there is to be understood by a protecting group, such as especially a carboxy-protecting group, expressly also a polymeric carrier that is bonded to the functional group to be protected, such as, especially, the carboxy group, in such a manner that it can readily be removed, as is suitable, for example, for the Merrifield synthesis. A suitable polymeric carrier of this type is, for example, a polystyrene resin weakly crosslinked by copolymerisation with divinylbenzene, which resin carries bridge members suitable for reversible bonding of the peptide residues.

The reaction can be carried out in a manner known per se, the reactions conditions depending especially on whether and how the carboxy group that participates in the reaction is activated, customarily in the presence of a suitable solvent or diluent or a mixture thereof, and, if necessary, in the presence of a condensation agent which, for example, if the carboxy group that participates in the reaction is present in the form of an anhydride, may also be an acid-binding agent, while cooling or heating, for example in a temperature range of from approximately −30° C. to approximately +150° C., in a closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-N'-(3-dimethylaminopropyl) carbodiimide, suitable carbonyl compounds, for example carbonyldiimidazole, or 1,2-oxazolium compounds, for example 2-ethyl-5-phenyl-1,2-oxazolium-3'-sulphonate and 2-tert.-butyl-5-methylisoxazolium perchlorate, or a suitable acylamino compound, for example 2-ethoxy-1-ethoxycarbonyl-1,2-dihydroquinoline. Customary acid-binding condensation agents are, for example, alkali metal carbonates or bicarbonates, for example sodium or potassium carbonate or bicarbonate (customarily together with a sulphate), or organic bases, such as, customarily, sterically hindered tri-lower alkylamines, for example N,N-diisopropyl-N-ethylamine.

The removal of the protecting groups, for example the carboxy-, amino-, hydroxy-, carboxylic acid amide- or mercapto-protecting groups, is carried out in a manner known per se, for example by means of solvolysis, especially hydrolysis, alcoholysis or acidolysis, or by means of reduction, especially hydrogenolysis or chemical reduction, optionally in stages or simultaneously, it also being possible to use enzymatic methods.

Thus, tert.-lower alkoxycarbonyl, or lower alkoxycarbonyl substituted in the 2-position by an organic silyl group or in the 1-position by lower alkoxy or lower alkylthio, or optionally substituted diphenylmethoxycarbonyl can be converted into free carboxy, for example, by treatment with a suitable acid, such as formic acid or trifluoroacetic acid, optionally with the addition of a nucleophilic compound, such as phenol or anisole. Optionally substituted benzyloxycarbonyl can be freed, for example, by hydrogenolysis, that is to say by treatment with hydrogen in the presence of a metallic hydrogenation catalyst, such as a palladium catalyst. In addition, suitably substituted benzyloxycarbonyl, such as 4-nitrobenzyloxycarbonyl, can be converted into free carboxy also by chemical reduction, for example by treatment with an alkali metal dithionite, for example sodium dithionite, or with a reducing metal, for example zinc, or a reducing metal salt, such as a chromium-(II) salt, for example chromium(II) chloride, usually in the presence of an agent that yields hydrogen and that, together with the metal, is capable of producing nascent hydrogen, such as an acid, especially a suitable carboxylic acid, such as a lower alkanecarboxylic acid optionally substituted, for example, by hydroxy, for example acetic acid, formic acid, glycolic acid, diphenylglycolic acid, lactic acid, mandelic acid, 4-chloromandelic acid or tartaric acid, or an alcohol or thiol, water preferably being added. By treatment with a reducing metal or metal salt, as described above, it is also possible to convert 2-halo-lower alkoxycarbonyl (optionally after conversion of a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide.

A protected amino group is freed in a manner known per se and, depending on the nature of the protecting groups, by various methods, but preferably by solvolysis or reduction. 2-halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Optionally substituted diphenylmethoxycarbonylamino, tert.-lower alkoxycarbonylamino or 2-trisubstituted silylethoxycarbonylamino can be cleaved by treatment with a suitable acid, for example formic acid or trifluoroacetic acid, optionally substituted benzyloxycarbonylamino can be cleaved, for example, by hydrogenolysis, that is to say by treatment with hydrogen in the presence of a suitable hydrogenation catalyst, such as a palladium catalyst, optionally substituted triarylmethylamino or formylamino can be cleaved, for example, by treatment with an acid, such as a mineral acid, for example hydrochloric acid, or an organic acid, for example formic, acetic or trifluoroacetic acid, optionally in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and by subsequent solvolysis, such as alcoholysis or hydrolysis, of the resulting condensation product. An amino group protected by 2-substituted silylethoxycarbonyl can also be converted into the free amino group by treatment with a salt of hydrofluoric acid yielding fluoride anions, as indicated above in connection with the freeing of a correspondingly protected carboxy group.

Amino protected in the form of an azido group is converted into free amino, for example, by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively while cooling or heating.

A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group etherified by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Two hydroxy groups that are together protected by a preferably substituted methylene group, such as by lower alkylidene, for example isopropylidene, cycloalkylidene, for example cyclohexylidene, or benzylalkylidene, can be freed by acid solvolysis, especially in the presence of a mineral acid or a strong organic acid.

A carboxylic acid amide group protected by 9-xanthenyl is freed, for example, with hydrogen bromide in glacial acetic acid or with hydrogen fluoride in the presence of anisole.

A carboxylic acid amide group protected by mono-, di- or tri-arylmethyl can be freed, for example, with hydrogen fluoride in the presence of anisole; furthermore, a diphenylmethyl protecting group can be removed, for example, by hydrogenolysis in the presence of a palladium-on-carbon catalyst, and a di(4-methoxyphenyl)methyl protecting group or a 2,4,6-trimethoxybenzyl protecting group can be removed, for example, by means of trifluoroacetic acid. Also, a diarylmethyl protecting group in which one aryl radical is linked to a polymeric carrier can be removed with hydrogen fluoride in the presence of anisole.

If desired, if several protected functional groups are present, the protecting groups are so selected that more than one of these protecting groups can be removed at the same time, for example by acidolysis, such as by treatment with trifluoroacetic acid or formic acid, or by reduction, such as by treatment with zinc and acetic acid, or with hydrogen and a hydrogenation catalyst, such as a palladium-on-carbon catalyst.

Reaction variant (a) includes expressly also the embodiment of the process for the manufacture of peptideamides in which the terminal carboxy group of the peptide is removed from a polymeric carrier with the aid of ammonia and in the course of this is converted, as it were in situ, into the amide. In this case ammonia is the complementary fragment having a free amino group.

Process (b):

Suitable oxidising agents for the oxidation of mercapto groups for the purpose of linking disulphide bonds are, for example, atmospheric oxygen, which is preferably passed through an aqueous solution of the polypeptide to which a catalytic amount of a transition metal salt, for example iron(III) sulphate, iron(III) chloride or copper(II) sulphate, has optionally been added; iodine, also in the form of the potassium iodide adduct $KI_3$, which is preferably used in alcoholic, for example methanolic, or aqueous-alcoholic, for example aqueous-methanolic, solution; potassium hexacyanoferrate(III) in aqueous solution; 1,2-diiodoethane or azodicarboxylic acid dimethyl ester or diethyl ester which are reacted in water or in a mixture consisting of water and a water-miscible alcohol, for example methanol. The oxidation is preferably carried out at room temperature.

A mercapto-protecting group that can be removed under the reaction conditions and that is suitable for process (b) is, for example, acetylaminomethyl. In the case of the acetylaminomethyl protecting group, process (b) is advantageously carried out in acetic acid to which a small amount of hydrochloric acid has been added, using iodine as oxidising agent, for example as described in the Examples.

Process (c)

The functional groups that come into consideration, their protection and deprotection again by removal of the protecting groups, are described in process (a). Process (c) includes expressly also the removal of protecting groups that are bonded to a carrier that can be used, for example, in the Merrifield synthesis. In this case process (c) includes, therefore, the removal of the peptide or peptide-amide from the carrier.

Process (d)

Host cells suitable for transformation are, for example, microorganisms, such as yeasts, for example *Saccharomyces cerevisiae*, and especially bacterial strains that have no restriction or modification enzyme, especially strains of *Escherichia coli*, for example *E. coli* X1776, *E. coli* HB101, *E. coli* W3110, *E. coli* HB101/LM1035, *E. coli* JA221 (J. Clarke and J. Carbon, J. Mol. Biol. 120, 517 [1978]) or *E. coli* K12 strain 294, *Bacillus subtilis*, *Bacillus stearothermophilus*. Pseudomonas, Haemophilus, Streptococcus, and others, and also cells of higher organisms, especially established human or animal cell lines. Preferred host cells are the mentioned strains of *E. coli*, especially *E. coli* HB101 and *E. coli* JA221.

There are suitable, in principle, all those vectors which replicate and express in the selected host the heterologous DNA sequences according to the invention that code for the amino acid sequences according to the invention.

Examples of vectors that are suitable for the expression of a CGRP gene in an *E. coli* strain are bacteriophages, for example derivatives of the bacteriophage λ, or preferably plasmids, such as, especially, the plasmid colE1 and its derivatives, for example pMB9, pSF2124, pBR317 or pBR322. The preferred vectors of the present invention are derived from plasmid pBR322. Suitable vectors contain a complete replicon and a marker gene that renders possible the selection and identification of the microorganisms transformed by the expression plasmids by means of a phenotype feature. Suitable marker genes impart to the microorganism, for example, resistance to heavy metals, antibiotics and the like. Furthermore, preferred vectors of the present invention contain outside the replicon and marker gene regions recognition sequences for restriction endonucleases, so that the DNA sequence coding for the amino acid sequences according to the invention and optionally the expression control sequence can be inserted at these sites. The preferred vector, plasmid pBR322, contains an intact replicon, marker genes ($tet^R$ and $amp^R$) imparting resistance to tetracycline and ampicillin, and a series of recognition sequences, occurring only once, for restriction endonucleases, for example PstI (cleaves in the $amp^R$ gene, the $tet^R$ gene remains intact), BamHI, HindIII, SalI (all cleave in the $tet^R$ gene, the $amp^R$ gene remains intact), NruI and EcoRI.

Several expression control sequences can be used for regulating the CGRP expression. Especially expression control sequences of strongly expressed genes of the host cell to be transformed are used. When using pBR322 as hybrid vector and *E. coli* as host microorganism, suitable expression control sequences (which inter alia contain the promotor and the ribosomal binding site) are those of the lactose operon, the tryptophan operon, the arabinose operon and the like, and of the β-lactamase gene, the corresponding sequences of the phage λN-gene or of the phage fd-layer protein gene, and others. Whereas the promotor of the β-lactamase gene (β-lac-gene) is already contained in the plasmid pBR322, the other expression control sequences must be introduced into the plasmid. In the present invention, the preferred expression control sequence is that of the tryptophan operon (trp po).

Vectors suitable for replication and expression in yeast contain a yeast-replication origin and a selective genetic marker for yeast. Hybrid vectors that contain a yeast replication origin, for example the chromosomal autonomously replicating segment (ars), are retained extrachromosomally within the yeast cell after transformation and are replicated autonomously during mitosis. Also, hybrid vectors that contain sequences homologous to the yeast 2μ plasmid DNA can be used. Such hybrid vectors are integrated by recombination in 2μ plasmids already present within the cell, or replicate autonomously. 2μ sequences are especially suitable for plasmids having a high transformation frequency and permit a high copy number. Suitable marker genes for Yeast are especially those that impart antibiotic resistance to the host or, in the case of auxotrophic yeast mutants, genes that complement the host lesions. Corresponding genes impart, for example, resistance to the antibiotic cycloheximide or provide for prototrophy in an auxotrophic yeast mutant, for example the URA3, LEU2, HIS3 or, especially, the TRP1 gene. Preferably, yeast hybrid vectors furthermore contain a replication origin and a marker gene for a bacterial host, especially *E. coli*, so that the construction and the cloning of the hybrid vectors and their precursors can be carried out in one bacterial host. Expression control sequences suitable for expression in yeast are, for example, those of the TRP1, ADHI, ADHII, PHO3 or PHO5 gene, and also promotors involved in glycolysis, for example the PGK and the GAPDH promotor.

Especially suitable are expression vectors capable of replication and phenotypic selection that contain an expression control sequence and a DNA sequence coding for one of the amino acid sequences according to the invention, wherein the said DNA sequence together with transcription start signal and termination signal and translation start signal and stop signal in the said expression plasmid is so arranged, with regulation of the said expression control sequence, that the amino acid sequence according to the invention in question is expressed in a host cell transformed with the said expression plasmid.

In order to achieve effective expression, the gene coding for one of the amino acid sequences according to the invention must be correctly arranged ("in phase") with the expression control sequence. It is advantageous to link the expression control sequence into the region between the main mRNA origin and the ATG of the gene coding sequence, which is naturally linked to the expression control sequence (for example the β-lac coding sequence when using the β-lac promotor), with the gene coding for the amino acid sequence in question, which gene preferably has its own translation start signal (ATG) and translation stop signal (for example TAG). An effective transcription and translation is thus ensured.

For example, a vector, especially pBR322, is cleaved with a restriction endonuclease and, optionally after modification of the resulting linearised vector, an expression control sequence provided with corresponding restriction ends is introduced. The expression control sequence contains at the 3'-end (in the translation direction) the recognition sequence of a restriction endonuclease, so that the vector already containing the expression control sequence can be digested with the said restriction enzyme, and the gene coding for the amino acid sequence according to the invention in question provided with matching ends can be inserted. The result is a mixture of two hybrid plasmids which contain the gene in the correct and in the incorrect orientation, respectively. It is advantageous to cleave the vector already containing the expression control sequence with a second restriction endonuclease within the vector DNA and to insert into the resulting vector fragment the gene coding for the amino acid sequence according to the invention in question provided with correct ends. All operations on the vector are carried out preferably in such a manner that the function of the replicon and of at least one marker gene is not impaired.

In a preferred embodiment of the present invention, a vector derived from pBR322 that contains an expression control sequence, especially that of the tryptophan operon (trp po), which at the 3'-end (between the main mRNA origin and the first ATG) carries the recognition sequence for a restriction endonuclease preferably forming cohesive ends, for example EcoRI, is digested with the mentioned restriction endonuclease and, in the vector DNA fragment, with a second restriction endonuclease that forms blunt, or preferably cohesive, ends, for example BamHI, after which the so linearised vector is linked with the gene having corresponding ends (for example with an EcoRI end before the ATG start and a BamHL end after the translation stop codon) that codes for one of the amino acid sequences according to the invention. The linking is carried out in known manner by pairing the complementary (cohesive) ends and ligation, for example with $T_4$ DNA ligase.

The CGRP gene, obtained synthetically or from genomic DNA by the mRNA route, and provided with corresponding cohesive (especially EcoRI and BamHI) ends can, before introduction into an expression plasmid, also be cloned into a vector, for example pBR322, in order to obtain larger amounts of CGRP gene, for example for the sequence analysis. The isolation of the clones that contain the hybrid plasmid is carried out, for example, with a CGRP-specific, radioactively labelled oligodeoxynucleotide probe. The characterisation of the CGRP gene is effected, for example, in accordance with the method of Maxam and Gilbert [A. M. Maxam and W. Gilbert, Proc. Natl. Acad. Sci. USA 74, 560 (1977); see also Meth. Enzym. 65, 499 (1980)].

The transformation of the host cells with the expression plasmids according to the invention is carried out, for example, in the manner described in the literature, for example for *S. cerevisiae* [A. Hinnen et al., Proc. Natl. Acad. Sci. USA 75, 1929 (1978)], *B. subtilis* [Anagnostopoulus et al., J. Bacteriol. 81, 741 (1961)]and *E. coli* [M. Mandel et al., J. Mol. Biol. 53, 159 (1970)]. The isolation of the transformed host cells is effected advantageously from a selective nutrient medium to which there has been added the biocide against which the marker gene contained in the expression plasmid imparts resistance. If, as preferred, the expression plasmids contain the $amp^R$ gene, ampicillin is accordingly added to the nutrient medium. Cells that do not contain the expression plasmid are destroyed in such a medium.

The invention relates also to the transformed host cells obtainable in the manner mentioned which are capable of producing the peptides according to the invention.

The cultivation of the transformed host cells according to the invention in accordance with process (d) is effected in a manner known per se. For example, various carbon sources can be used for the cultivation of the transformed host microorganisms according to the invention. Examples of preferred carbon sources are assimilable carbohydrates, such as glucose, maltose, mannitol or lactose, or an acetate which can be used either alone or in suitable mixtures. Suitable nitrogen sources are, for example, amino acids, such as casamino acids, peptides and proteins and their degradation products, such as tryptone, peptone or meat extracts; also yeast extracts, malt extract, and also ammonium salts, for example ammonium chloride, sulphate or nitrate, which can be used either alone or in suitable mixtures. Inorganic salts, which can also be used, are, for example, sulphates, chlorides, phosphates and carbonates of sodium, potassium, magnesium and calcium.

Furthermore, the culture medium contains, for example, growth-promoting substances, such as trace elements, for example iron, zinc and manganese, and preferably substances that exert a selection pressure and prevent the growth of cells that have lost the expression plasmid. Thus, for example, ampicillin is added to the medium when the expression plasmid contains an $amp^R$ gene. Such an addition of antibiotically active substances also has the effect of destroying contaminating antibiotic-sensitive microorganisms.

The cultivation is carried out in accordance with processes that are known per se. The cultivating conditions, such as temperature, pH value of the medium and fermentation time, are so selected that maximum titres of the peptides according to the invention are obtained. Thus, an *E. coli* or a yeast strain is preferably cultivated under aerobic conditions in submersed culture with shaking or stirring at a temperature of, for example, from 20° to 40° C., preferably approximately 30° C., and a pH value of from 4 to 9, preferably pH 7, for approximately from 4 to 20 hours, preferably from 8 to 12 hours. During cultivation, the expression product (CGRP) accumulates intracellularly.

The N-terminal methionine can in certain host cells be removed post-translationally. Furthermore, in certain host cells the N-terminal amino acid can be acetylated.

When the cell density has reached an adequate value, the cultivation is terminated and the peptide according to the invention is freed from the cells of the microorganism. For this purpose the cells are destroyed, for example by treatment with a detergent, such as SDS or Triton, or are lysed with lysozyme or a similarly acting enzyme. Alternatively, or in addition, mechanical forces, such as shearing forces (for example X-press, French press, Dyno-mill) or shaking with glass beads or aluminium oxide, or alternate freezing, for example in liquid nitrogen, and thawing, for example to from 30° to 40° C., and ultrasound, can be used to break the cells. The resulting mixture, which contains proteins, nucleic acids and other cell constituents, after centrifuging is enriched in a manner known per se with regard to the protein content, including content of peptides according to the invention. Thus, for example, the non-protein constituents are for the most part removed by polyethyleneimine treatment and the proteins, including the peptides according to the invention, are precipitated, for example by saturating the solution with ammonium sulphate or with other salts. Bacterial proteins can also be precipitated by means of acidification with acetic acid (for example 0.1%, pH 4–5). A further enrichment of the peptides according to the invention can be achieved by extracting the acetic acid supernatant with n-butanol. Other purification steps include, for example, gel electrophoresis, chromatographic processes, such as ion exchange chromatography, size exclusion chromatography, HPLC, reverse phase HPLC and the like, separation of the constituents of the mixture according to molecular size by means of a suitable Sephadex® column, dialysis, affinity chromatography, for example with antibodies, especially monoclonal antibodies, and other processes, especially those known from the literature.

For example, the isolation of an expressed peptide according to the invention may comprise the following steps:

Separation of the cells from the culture solution by centrifugation;

Production of a crude extract by destroying the cells, for example by treatment with a lysing enzyme and-/or alternate freezing and thawing again;

Removal by centrifugation of the insoluble constituents;

Precipitation of the DNA by the addition of polyethyleneimine;

Precipitation of the proteins, including the peptides according to the invention, by ammonium sulphate;

Affinity chromatography of the dissolved precipitate on a monoclonal anti-CGRP antibody column;

Removal of salts from the resulting solution by means of dialysis or chromatography on Sephadex G25.

Alternatively, after separating off the DNA the bacterial proteins can be precipitated by means of 0.1% acetic acid and the peptide according to the invention concerned extracted from the acidic supernatant with n-butanol, or the acidic supernatant can be subjected directly to ion exchange chromatography (for example on carboxymethylcellulose). Other purification steps include gel filtration on Sephadex G50 (or G75), and reverse phase HPLC. Removal of salts is effected again on Sephadex G25.

A test with anti-CGRP antibodies (for example monoclonal antibodies obtainable from rabbits or from hybridoma cells) can be used to detect the peptides according to the invention.

Process e

An amino acid $AS^\Omega$ that can be degraded enzymatically to the $NH_2$ group of the terminal amide group of the desired peptide-amide is, for example, glycine. A suitable enzyme can in this case be obtained from hypophyses, preferably hypophyses of pigs, as described in A. F. Bradbury, M. D. A. Finnie and D. G. Smyth, Nature 298, 686–688 (1982).

An amino acid $AS^\Omega$ that can be substituted by ammonia in the presence of a suitable enzyme is, for example, tyrosine. A suitable enzyme in this case is, for example, carboxypeptidase Y (Carlsberg Biotechnology Ltd., Copenhagen, Denmark), cf. for example Klaus Breddam et al., Carlsberg Res. Commun. 46, 121–128 (1981).

Additional operations

Salts of compounds with the (partial-)sequence of the formula I and having salt-forming groups can be manufactured in a manner known per se. For example, salts of compounds with the partial sequence of the formula I that contain more acidic than basic groups can be formed, for example, by treatment with metal compounds, such as alkali metal salts of suitable organic carboxylic acids, for example the sodium salt of α-ethylcaproic acid, or with inorganic alkali metal or alkaline earth metal salts, for example sodium bicarbonate, or with ammonia or a suitable organic amine, there preferably being used stoichiometric amounts or only a small excess of the salt-forming agent. Acid addition salts of compounds with the sequence of the formula I are obtained in customary manner, for example by treatment with an acid or a suitable anion exchange reagent. Internal salts of compounds having the partial sequence of the formula I that contain, for example, a free carboxy group and a free amino group, can be formed, for example, by neutralising salts, such as acid addition salts, to the isoelectric point, for example with weak bases, or by treatment with liquid ion exchangers.

Salts can be converted in customary manner into the free compounds; metal and ammonium salts can be converted into the free compounds, for example, by treatment with suitable acids, and acid addition salts, for example, by treatment with a suitable basic agent.

The invention relates also to DNA sequences that code for the amino acid sequences of the peptides according to the invention.

The DNA sequences according to the invention contain as a partial sequence of a larger sequence a sequence of the formula IV d(GCETGYAAYACXGCEACXTGYGTXACXCAYNGKYTZGCEGGXYTZYTZQRSNGK      (IV)
   Ala Cys Asn Thr Ala Thr Cys Val Thr His Arg Leu Ala Gly Leu Leu Ser Arg QRSGGXGGXATGGTXAAMQRSAAYTTLGTXCCXACXAAYGTXGGXQRSAAMGCETTL)
Ser Gly Gly Met Val Lys Ser Asn Phe Val Pro Thr Asn Val Gly Ser Lys Ala Phe in which only the deoxynucleotide sequence of the coding strand, commencing with the 5'-end and, beneath that, the amino acids for which each triplet codes, are indicated, and in which:

A = adenosyl,
T = thymidyl,
G = guanosyl,
C = cytidyl,
E = A, T, C or G,
K = A, T, C or G when N = C, or
K = A or G when N = A,
L = T or C,
M = A or G,
N = A or C,
Q = T or A,
R,S: R = C and S = A, T, C or G when Q = T, or
   R = G and S = T or C when Q = A,
X = A, T, C or G,
Y = T or C, and
Z = A, T, C or G when Y = C, or
Z = A or G when Y = T, wherein the "d" standing before the bracket means that the nucleosides mentioned in the brackets are 2-deoxyribo-nucleosides.

The DNA sequences according to the invention contain preferably no more than 290, especially no more than 230, more especially no more than 200 and preferably no more than 150, for example 136, deoxynucleotides in the coding strand.

Advantageously, the ends of the DNA sequences according to the invention, as early as during their manufacture, are provided with radicals that render possible insertion into vectors, for example are provided with recognition sequences for restriction endonucleases, with the start codon ATG and a stop codon, for example TAG. If the later manufacture of peptide-amides is intended, the DNA sequence can be provided, for example, with a codon that codes for an amino acid that can later be enzymatically so degraded that the $NH_2$ group of the terminal amide group of the peptide-amide results therefrom. An amino acid that can be degraded in this manner is, for example, glycine. Alternatively, for the later manufacture of peptideamides, the DNA sequence can be provided with a codon that codes for an amino acid, such as, especially, tyrosine, which can be substituted by ammonia in the presence of a suitable enzyme, such as, especially, a suitable exopeptidase, for example carboxypeptidase Y.

The invention relates especially to the abovementioned DNA sequences that contain triplets that are preferred by *E. coli* and code for the amino acids of the peptides according to the invention. Such triplets are especially:

for alanine (Ala): GCT
arginine (Arg): CGT
glycine (Gly) GGT
cysteine (Cys): TGC
valine (Val): GTT
leucine (Leu): CTG
serine (Ser): TCT
threonine (Thr): ACC
phenylalanine (Phe): TTC
tyrosine (Tyr): TAC
methionine (Met): ATG
aspartic acid (Asp): GAC
glutamic acid (Glu): GAA
lysine (Lys): AAA
isoleucine (Ile): ATC
histidine (His) CAC
proline (Pro) CCG
glutamine (Gln) CAG
asparagine (Asn) AAC The preferred stop signal (NON) is the codon TAG.

Preferred are DNA sequences having up to 200, for example 136, deoxynucleotides in the coding strand, which contain the following DNA sequence in which only the coding strand, commencing with the 5'-end, is indicated, and, for the purpose of better understanding, also mentioned are the amino acids for which each triplet codes:

(1981)] use in solid phase synthesis instead of individual deoxynucleotides trideoxynucleotides linked by the phosphotriester method, which can then be condensed within a short time and in good yields, for example to form a polydeoxynucleotide with 31 bases. The authentic double-stranded DNA can be built up enzymatically from chemically produced short segments. H. G. Khorana et al. [J. Biol. Chem. 251, 565 (1976)] use for this purpose overlapping polydeoxynucleotide sequences from both DNA strands, which are held together in the correct arrangements by base pairing and are then chemically linked by the enzyme DNA ligase. A further possibility comprises incubating one polydeoxynucleotide sequence from each of the two DNA strands having a short overlapping segment, in the presence of the four required deoxynucleoside triphosphates, with a DNA polymerase, for example DNA polymerase I, Klenow fragment of polymerase I, T4 DNA polymerase, or with AMV (avian myeloblastosis virus) reverse transcriptase. In this process the two polydeoxynucleotide sequences are held together in the correct arrangement by base pairing and supplemented by the enzyme with the required deoxynucleotides to form a complete double-stranded DNA [S. A. Narang et al., Anal. Biochem. 121, 356 (1982)]. K. Itakura et al. [J. Biol. Chem. 257, 9226 (1982)] describe how, based on this principle, a 132 base pair-long segment of the human leucocyte interferon $\alpha_2$-gene can be built up in the presence of DNA polymerase I (Klenow fragment) from 4 chemically synthesised fragments having a length of from 39

Ala Cys Asn Thr Ala Thr Cys Val Thr His Arg Leu Ala Gly Leu Leu Ser Arg     (IVa)
d(GCCTGCAACACTGCCACCTGTGTGACTCATCGGCTGGCAGGCTTGCTGAGCAGA

Ser Gly Gly Met Val Lys Ser Asn Phe Val Pro Thr Asn Val Gly Ser Lys Ala Phe
TCAGGGGGCATGGTGAAGAGCAACTTCGTGCCCACCAATGTGGGTTCCAAAGCCTTT)

Especially preferred for expression in *E. coli* are DNA sequences having up to 200, for example 136, deoxynucleotides in the coding strand, which contain the following DNA sequence, wherein only the coding strand, commencing with the 5'-end, is indicated, and, for the purpose of better understanding, the amino acids for which each triplet codes are also mentioned:

to 42 bases, achieving a 40% saving of chemical synthesis by comparison with the above-described method in which only ligase is used.

The process for the synthesis of the DNA sequences according to the invention described in this application is characterised in that (α) a suitably protected deoxynucleoside is bonded to a Ala Cys Asn Thr Ala Thr Cys Val Thr His Arg Leu Ala Gly Leu Leu Arg     (IVb)
d(GCTTGCAACACCGCTACCTGCGTTACCCACCGTCTGGCTGGTCTGTCTCGT Ser Gly Gly Met Val Lys Ser Asn Phe Val Pro Thr Asn Val Gly Ser Lys Ala Phe
TCTGGTGGTATGGTTAAATCTAACTTCGTTCCGACCAACGTTGGTTCTAAAGCTTTC)

The DNA sequences according to the invention are manufactured according to processes known per se.

Methods of synthesising DNA have been summarised by S. A. Narang [Tetrahedron 34, 3(1983)]. The known synthesising techniques permit the manufacture of polydeoxynucleotides having a length of towards 20 bases in a good yield, high purity and in a relatively short time. Suitably protected deoxynucleotides are linked with one another by the phosphodiester method [K. L. Agarwal et al., Angew. Chem. 84, 489 (1972)], or the even more efficient phosphotriester method [C. B. Reese, Tetrahedron 34, 3143 (1972)] or phosphite triester method [R. L. Letsinger and W. B. Lunsford, J. Am. Chem. Soc. 98, 3655 (1976)]. Simplification of the synthesis of oligo- and poly-deoxynucleotides is rendered possible by the solid phase method in which the deoxynucleotide chains are bonded to a suitable polymer. K. Itakura et al. [J. Am. Chem. Soc. 103, 706 solid carrier, (β) suitably protected di-, tri- or tetra-deoxynucleotides are manufactured according to the phosphotriester or phosphite method, (γ) a deoxynucleoside or oligodeoxynucleotide bonded to the carrier is linked with suitably protected monodeoxynucleotides or di-, tri- or tetra-deoxynucleotides (produced according to (β)) in accordance with the phosphotriester or the phosphite method, (δ) oligodeoxynucleotides obtainable according to (γ) which are bonded to carriers and have the desired number of bases are removed from the carrier, if desired purified, freed of protecting groups, and the free 5'-terminal hydroxy groups are phosphorylated, (ε) 2 oligodeoxynucleotides obtained in accordance with (δ) from the coding and from the complementary strand having at least 3, and preferably from 8 to 15, overlapping base pairs are annealed and are supplemented with a DNA polymerase in the presence of the four deoxynucleoside triphosphates to form a double-stranded DNA segment that contains the CGRP gene, and are linked using a ligase to form the desired structural gene.

The synthesis of the DNA sequence of formula IV can accordingly be carried out, for example, by building up two oligodeoxynucleotides, namely a negative and a positive strand having approximately the same number of bases, these oligodeoxynucleotides having the capability in a partial region of forming hydrogen bonds with each other, by means of condensing trinucleotide blocks, in stages, onto a growing nucleotide sequence according to the solid phase process, by detaching the individual nucleotide chains from the solid carrier, removing any protecting groups present, carrying out purification, for example by means of gel-electrophoresis, and, after kinasing and hybridising, making up to the complete DNA duplex, preferably by means of DNA polymerase I (Klenow fragment).

A plurality of solid carrier materials can be used in step ($\beta$), such as polystyrene of various crosslinkages and swelling properties, polyacrylamides, polyacrylamide copolymers, polyamides supported on inorganic material such as kieselguhr, silica gel or Alox, or functionalised silanes. In a preferred embodiment the solid carrier materials used are crosslinked polystyrenes, which are linked in a manner known per se with the 5'-OH group of suitably protected deoxynucleosides by way of "spacers", such as alkylene groups having from 2 to 12 carbon atoms interrupted by from 1 to 5 polar divalent functional groups, such as imino, oxo, thio, oxocarbonyl or amidocarbonyl. Especially preferred is the reaction with succinic acid anhydride of nucleosides of the formula V protected in the 5'-position and optionally in the base moiety, in which $R^1$ represents a protecting group that can be removed by acid, such as a triarylmethyl protecting group, for example a 4-methoxytrityl group or a 4,4'-dimethoxytrityl group, or a tri-lower alkylsilyl protecting group, for example a tert.-butyldimethylsilyl group, and in which Ba represents an optionally protected base selected from the group comprising thymyl, cytosyl, adenyl and guanyl, optionally in the presence of bases, such as pyridine, triethylamine or dimethylaminopyridine, followed by reaction with aminomethylated polystyrene that is crosslinked by from 0.5 to 2% divinylbenzene, with the aid of reagents that activate the carboxylic acid radical, preferably N-hydroxysuccinimide, or p-nitrophenol and dehydrating agents, such as carbodiimides, for example dicyclohexylcarbodiimide (scheme 1). In scheme 1 and in the following the deoxyribose residue is often represented in the customary condensed form.

The reaction is carried out in an inert aprotic solvent, for example pyridine, tetrahydrofuran, dioxan, ethyl acetate, chloroform, methylene chloride, dimethylformamide or diethylacetamide, or in mixtures thereof, at room temperature or at slightly elevated or reduced temperature, for example in a temperature range of from approximately $-10°$ C. to approximately 50° C., preferably at room temperature, it being possible for the reaction in the presence of a dehydrating agent also to be carried out at a lower temperature, for example at approximately 0° C.

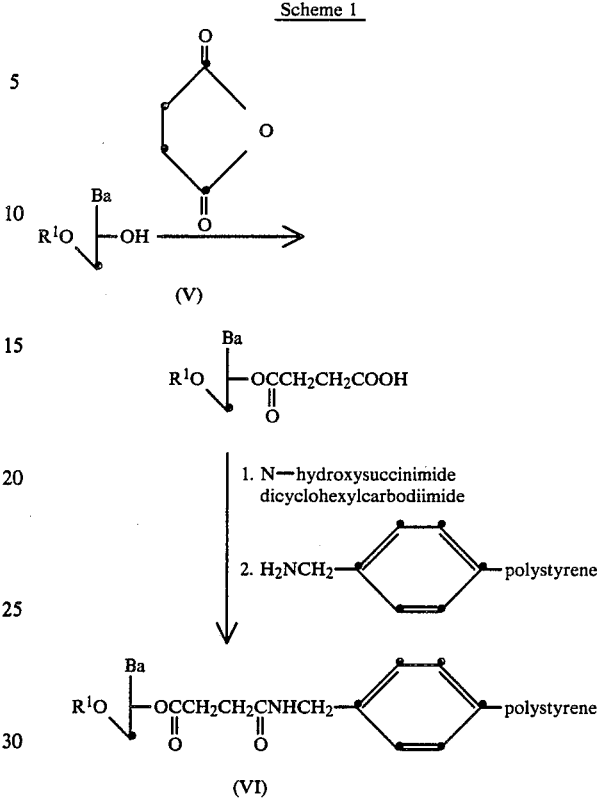

In the manufacture in accordance with the invention of di-, tri- or tetra-nucleotides according to step ($\beta$) (scheme 2), nucleosides of the formula V protected in the 5'-position and optionally in the base moiety, in which $R^1$ and Ba have the meanings given above, are reacted, optionally in the presence of dehydrating agents or in the presence of bases, with activated phosphoric esters of the formula VII, in which each of $X^1$ and $X^2$, independently of the other, represents hydroxy or a salt derived therefrom, halogen, imidazolyl, 1,2,4-triazol-1-yl, tetrazolyl or 1-benztriazolyloxy, and $X^2$ in addition also represents 2-cyanoethoxy, 2-trihaloethoxy, 2-arylsulphonylethoxy, 2-lower alkylthioethoxy, 2-arylthioethoxy or 2-(4-nitrophenyl)ethoxy, and $R^2$ represents a protecting group that can be removed by a base or by a nucleophilic compound, such as by ammonium hydroxide, thiophenolate or by an aryl aldoximate, such as phenyl optionally substituted by halogen, nitro and/or by lower alkyl, methyl, or benzyl optionally substituted by nitro, or represents a protecting group that can be removed by metal ions, such as 8-quinolyl or 5-chloro-8-quinolyl.

Subsequently, a resulting compound of the formula VIII, in which $R^1$, $X^2$ and $R^2$ have the meanings given above, is first optionally reacted with a 2-substituted ethanol, which converts the radical $X^2$ into a group $OR^3$ in which $R^3$ represents cyanoethyl, 2-trihaloethyl, 2-arylsulphonylethyl, 2-lower alkylthioethyl, 2-arylthioethyl or 2-(4-nitrophenyl)-ethyl, and then the protecting group $R^1$ is removed, and the resulting compound of the formula IX is reacted with another compound of the formula VIII, optionally in the presence of dehydrating agents or in the presence of bases, to form a dinucleotide X (scheme 2). Optionally, a compound of the formula VIII is converted by reaction with bases and water into a different compound of the formula VIII in which $X^2$ represents hydroxy or a salt derived therefrom.

The reactions are carried out in one of the above-mentioned inert solvents at room temperature or slightly elevated or reduced temperature, for example at room temperature.

The removal of the protecting group $R^1$ is carried out, for example, by means of acids, such as a mineral acid, for example hydrochloric acid or sulphuric acid, a carboxylic acid, for example acetic acid, trichloroacetic acid or formic acid, a sulphonic acid, for example methane- or p-toluene-sulphonic acid, or especially a Lewis acid, for example zinc chloride, zinc bromide, aluminium chloride, a dialkylaluminium halide, for example dibutyl- or diethyl-aluminium chloride, or boron trifluoride, at from 10° C. to 50° C., especially at room temperature. When using a dialkylaluminium halide, the removal is carried out in a lipophilic solvent, especially in toluene and, when using another of the mentioned Lewis acids, in a solvent mixture consisting of a halogenated hydrocarbon, for example methylene chloride, and a lower alkanol, for example ethanol or isopropanol.

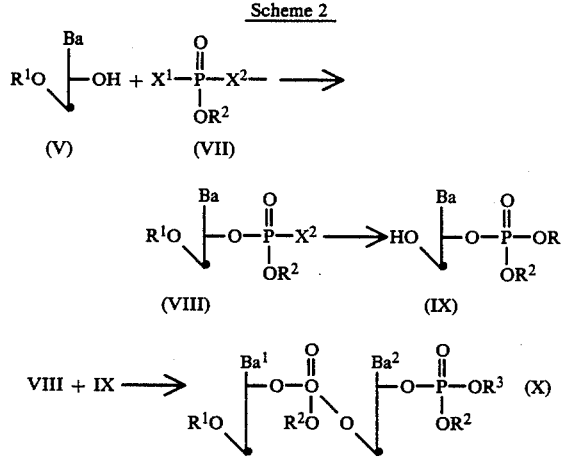

Dinucleotides of the formula X can also be manufactured by reacting nucleosides of the formula V, in which $R^1$ and Ba have the meanings given above, with phosphites of the formula VIIA in which $X^1$ represents halogen, especially chlorine, $X^2$ represents halogen, especially chlorine, or di-lower alkylamino, especially dimethylamino or diisopropylamino, or morpholino, piperidino or pyrrolidino, and $R^2$ has the meaning given above for formula VII, especially methyl, optionally in the presence of a suitable base (scheme 3). The resulting compound of the formula VIIIA either is reacted with a 2-substituted ethanol, which converts the radical $X^2$ into a group $OR^3$ in which $R^3$ has the meanings given above, and is then oxidised with an oxidising agent, for example iodine in the presence of a base, to form the phosphate, and the protecting group $R^1$ is removed, yielding a compound of the formula IX, or is reacted with a compound of the formula IX, then oxidised with an oxidising agent, for example iodine in the presence of a base, to form a compound of the formula

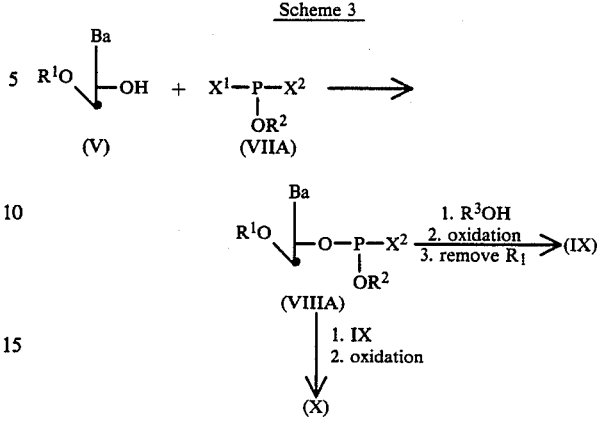

For the manufacture of trinucleotides, the protecting group $R^1$ in dinucleotides of the formula X, in which $R^1$, $R^2$ and $R^3$ have the meanings given above and each of $Ba^1$ and $Ba^2$, independently of the other, represents thymyl, cytosyl, adenyl or guanyl, is removed, and the resulting compound is reacted with a compound of the formula VIII, optionally in the presence of dehydrating agents or in the presence of bases, or with a compound of the formula VIIIA followed by oxidation, yielding a compound of the formula XI (scheme 4). The removal of the protecting group $R^1$ and the condensation to form the trinucleotides of the formula XI are carried out in the same manner as described for the manufacture of the dinucleotides of the formula X.

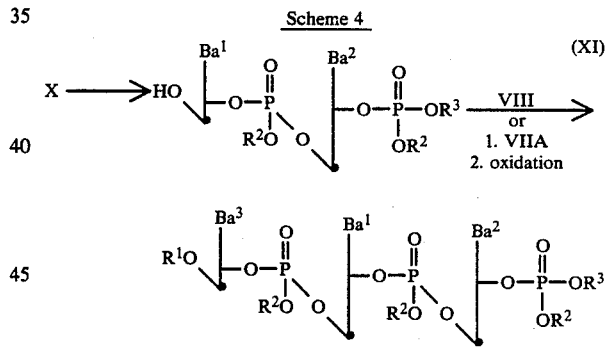

For the manufacture of tetranucleotides, trinucleotides of the formula XI are reacted as described above for dinucleotides of the formula X.

In a preferred arrangement there is used as protecting group $R^1$ a 4-methoxytrityl group, as protecting group $R^2$ a phenyl group substituted by chlorine, especially 2-chlorophenyl, and as protecting group $R^3$ a 2-cyanoethyl group. 1-Benztriazolyloxy is preferred as radical $X^1$ and $X^2$ in the compound of the formula VII.

Trinucleotides of the formula XI are preferably manufactured by removing the protecting group $R^1$ from dinucleotides of the formula X and reacting the resulting compound with a compound of the formula VIII in which $X^2$ represents hydroxy or a salt derived therefrom, in the presence of a dehydrating agent (scheme 4). Dehydrating agents according to the invention are, for example, 2,4,6-trimethylbenzenesulphonyl or triisopropylbenzenesulphonyl chloride, imidazole, tetrazole or 1,2,4-triazole, optionally substituted by nitro. 1-

(2,4,6-trimethylbenzenesulphonyl)-3-nitro-1,2,4-triazole (XII) is preferred as dehydrating agent.

The nucleosides used are preferably those in which the free amino group is protected in the base moiety. Preferred protecting groups are benzoyl for adenine, benzoyl or 4-methoxybenzoyl for cytosine, and isobutyryl or diphenylacetyl for guanine. Thymine is preferably used without a protecting group.

In the manufacture of oligonucleotides in accordance with step ($\gamma$), an apparatus that is known per se with a semi-automatic or fully automatic, microprocessor-controlled feed system for solvents and reagents is used. In a compound of the formula VI produced according to step ($\alpha$), the protecting group $R^1$ is removed as described above and the resulting compound is then reacted, optionally in the presence of a dehydrating agent or in the presence of a base, either with a compound of the formula VIII, or with a compound of the formula VIIIA, or with a compound of the formula X or XI, in which the protecting group $R^3$ has previously been removed with bases (a group 2-cyanoethyl as $R^3$ is removed, for example, with a tri-lower alkylamine, for example triethylamine, in one of the above-mentioned inert solvents or solvent mixtures at from 10° C. to 40° C., especially at room temperature). Instead of dinucleotide of the formula X or a trinucleotide of the formula XI it is possible to use a tetranucleotide produced in accordance with step ($\beta$). If a phosphite of the formula VIIIA is used, subsequent treatment with an oxidising agent, for example iodine in the presence of a base, is carried out. The compound of the formula XIII produced in this manner, in which $R^1$, $R^2$ and Ba have the meanings given above and n is an integer of from 1 to 4, is subjected to the reaction steps described for the compound of the formula VI (removal of $R^1$, reaction with VIII, VIIIA, X, XI or the corresponding tetranucleotide, optionally with oxidative after-treatment) as often as is necessary to produce a compound of the formula XIII (n is an integer).

azole, tetrazole or 1,2,4-triazole optionally substituted by nitro. Especially preferred is 1-(2,4,6-trimethylbenzenesulphonyl)-3-nitro-1,2,4-triazole (XII).

The especially preferred combination, comprising using as protecting group $R^1$ a 4-monomethoxytrityl group, using zinc bromide in the presence of 1,2,4-triazole to remove $R^1$, and using a triazole of the formula XII as dehydrating agent for the reaction of oligonucleotide-polystyrene resin of the formula XIII from which the protecting group has been removed with a trinucleotide of the formula XI from which the protecting group has been removed, makes it possible for even long nucleotide chains to be produced within a short time, in high yields and with high purity.

Processes that are known per se are used for the removal of oligodeoxynucleotides from the carrier and for the removal of the protecting groups in accordance with step ($\delta$). An especially preferred reagent for the removal from the carrier and for the removal of the preferred 2-chlorophenyl protecting group is an aryl aldoximate, for example 1,1,3,3-tetramethylguanidinium 2-nitrobenzaldoximate. The reaction is carried out in one of the above-mentioned inert solvents to which some water has been added, for example in 95% strength pyridine, at room temperature. Subsequently, reaction with aqueous ammonia at room temperature or elevated temperature, for example at from 20° C. to 70° C., especially at 50° C., is carried out.

For the ligation of the oligodeoxynucelotides, a phosphate radical is introduced at the 5'-terminal hydroxy group in accordance with step ($\delta$). The introduction of the phosphate radical (phosphorylation) is carried out in a manner known per se using $T_4$ polynucleotide kinase in the presence of ATP.

Oligodeoxynucelotides produced as described above consisting of the coding and the complementary DNA strand contain overlapping sequences consisting of at least 3, and preferably from 8 to 15, overlapping base pairs. Such oligodeoxynucelotide pairs are held to-

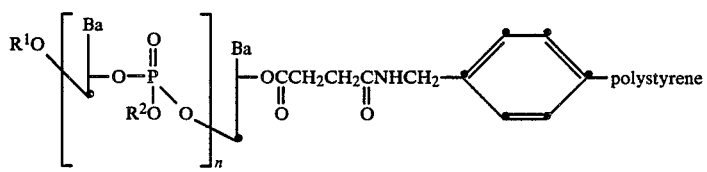

(XIII)

In a preferred embodiment of the invention, 4-methoxytrityl is used as protecting group $R^1$ and the removal of this group is carried out with zinc bromide in the presence of a CH- or NH-acid compound, especially 1,2,4-triazole or tetrazole. The use of, for example, 1,2,4-triazole for the removal of the 4-methoxytrityl protecting group is novel, and surprisingly results in the removal being quick and producing high yields without side reactions. Especially preferred is the use of zinc bromide and 1,2,4-triazole in a molar ratio of between 20:1 and 100:1 in a solvent mixture consisting of an aprotic solvent and an alcohol, for example methylene chloride and 2-propanol.

In a preferred embodiment, a compound of the formula VI or of the formula XIII in which the protecting group $R^1$ has been removed, is reacted with a trinucleotide of the formula XI in which the protecting group $R^3$ has been removed, in the presence of a dehydrating agent, such as, for example, 2,4,6-trimethylbenzenesulphonyl or triisopropylbenzenesulphonyl chloride, imidgether during mixing by hydrogen bonding. The projecting single-stranded ends act in accordance with step ($\epsilon$) as a matrix (template) for the synthesis of the complementary strand using a DNA polymerase, for example DNA polymerase I, Klenow fragment of DNA polymerase I or $T_4$ DNA polymerase, or using AMV reverse transcriptase, in the presence of the four deoxynucleoside triphosphates (dATP, dCTP, dGTP and TTP). The duplex DNAs formed during complementing have blunt ends.

The DNA sequences obtainable in accordance with process step ($\epsilon$) contain at the ends nucleotide sequences that can be recognised and cleaved by restriction endonucleases. Depending on the choice of nucleotide sequences and accordingly of the restriction endonucleases, during the cleavage completely base-paired (blunt) ends or ends with an overlapping DNA strand (staggered ends) are formed.

The invention relates also to pharmaceutical preparations that contain as active ingredient an effective dose, especially a dose effective for the treatment of the above-mentioned diseases, of one of the peptide-amides according to the invention or a salt thereof together with a significant amount, that is to say more than 50% by weight, preferably more than 95% by weight, especially more than 99% by weight, of a pharmaceutical carrier, especially such preparations for intranasal or parenteral, such as intramuscular or intravenous, administration to warm-blooded animals, such as, most especially, humans.

The dosage of the active ingredient depends on the species of the warm-blooded animal, the body weight, age and individual condition, the disease to be treated and the mode of administration.

The novel pharmaceutical preparations for parenteral administration contain, in the form ready for use, from approximately 0.001 part per thousand by weight to approximately 1 part per hundred by weight, preferably from approximately 0.005 parts per thousand by weight to approximately 0.1 part per thousand by weight, for example 0.01 part per thousand by weight, of the active ingredient. The pharmaceutical preparations according to the invention may be, for example, in dosage unit form, such as in ampoule form.

Preferably, solutions of the active ingredient, and also suspensions, especially isotonic aqueous solutions or suspensions, are used, and these, for example in the case of lyophilised preparations that contain the active substance on its own or together with a carrier, for example mannitol, can be prepared before use. In particular for intranasal administration, suspensions in oil are especially suitable. The pharmaceutical preparations may be sterilised and/or contain adjuncts, for example preservatives, stabilisers, wetting and/or emulsifying agents, solubilisers, salts for regulating the osmotic pressure and/or buffers, and are manufactured in a manner known per se, for example by means of conventional dissolving or lyophilising processes. The mentioned solutions or suspensions may contain viscosity-increasing substances, such as sodium carboxymethylcellulose, carboxymethylcellulose, dextran, polyvinylpyrrolidone or, preferably, gelatine.

Suspensions in oil contain as oily components the vegetable, synthetic or semi-synthetic oils customary for injections purposes. As such there may be mentioned especially liquid fatty acid esters that contain as acid component a long-chain fatty acid having from 8 to 22, especially from 12 to 22, carbon atoms, such as, for example, lauric acid, tridecylic acid, myristic acid, pentadecylic acid, palmitic acid, margaric acid, stearic acid, arachidic acid, behenic acid or corresponding unsaturated acids, such as, for example, oleic acid, elaidic acid, erucic acid, brassidic acid or linoleic acid. The alcohol component has a maximum of 6 carbon atoms and is a mono- or poly-hydric, for example mono-, di- or tri-hydric alcohol, for example methanol, ethanol, propanol, butanol or pentanol or isomers thereof, but especially glycol or glycerin. There may therefore be mentioned by way of example as fatty acid esters: ethyl oleate, isopropyl myristate, isopropyl palmitate, "Labrafil M 2735" (polyoxyethyleneglycerin trioleate, Messrs. Gattefosseé, Paris), "Miglyol 812" (triglyceride of saturated fatty acids having a chain length of from $C_8$ to $C_{12}$, Messrs. Chemische Werke, Witten/Ruhr, Germany), but especially vegetable oils, such as cotton seed oil, almond oil, olive oil, castor oil, sesame oil, soya bean oil, and especially ground-nut oil.

The manufacture of the injection preparations is effected in customary manner under antimicrobial conditions, as is also the introduction thereof into ampoules or phials and the sealing of the containers.

The following Examples illustrate the invention. Temperatures are in degrees Celsius.

The $R_f$ values, unless states otherwise or unless obvious from the context, are ascertained on thin-layer silica gel plates in the following solvent system: I : dichloromethane/methanol (9:1).

Accordingly, for example $R_f$ (I) represents an $R_f$ value ascertained in the solvent system I.

Abbreviations abs. = absolute
Acm = acetamidomethyl
Boc = tert.-butoxycarbonyl
BSA = bovine serum albumin
BZL = benzyl
2CZ = 2-chlorobenzyloxycarbonyl
d = deoxy
DMF = dimethylformamide
DTT = 1,4-dithiothreitol (1,4-dimercapto-2,3-butanediol)
EDTA = ethylenediaminetetraacetic acid
EtBr = ethidium bromide
FAB = fast atom bombardment
Fmoc = 9-fluorenylmethoxycarbonyl
HPLC = high pressure liquid chromatography
HV = high vacuum
iBu = isobutyryl
M = molar
MBHA = mono-(4-methyl)-benzhydrylamine
Me = methyl
min. = minutes
mmt = (mono-4-methoxy)-trityl
MOB = 4-methoxybenzyl
MS = mass spectroscopy
Mtr = 4-methoxy-2,3,6-trimethylbenzenesulphonyl
N = normal
OD = optical density
RM = reaction mixture
RT = room temperature
SDS = sodium dodecyl sulphate
tBU = tertiary butyl
TNE = solution that contains 100 mM NaCl, 50 mM tris.HCl (pH 7.5) and 5 mM EDTA
TOS = 4-toluenesulphonyl
tris = tris-(hydroxymethyl)-aminomethane
tris.HCl = monohydrochloride of tris
rev/min = revolutions per minute
v or vol. = volume
XANT = 9-xanthenyl

EXAMPLE 1

A solution of 15 mg (3.8 μmol) of Ala-Cys(Acm)-Asn-Thr-Ala-Thr-Cys(Acm)-Val-Thr-His-Arg-Leu-Ala-Gly-Leu-Leu-Ser-Arg-Ser-Gly-Gly-Met-Val-Lys-Ser-Asn-Phe-Val-Pro-Thr-Asn-Val-Gly-Ser-Lys-Ala-Phe-NH$_2$ in 2.0 ml of 50% acetic acid is added dropwise within a period of 5 minutes at RT, while stirring, to a mixture of 0.26 ml of 0.1M iodine in glacial acetic acid, 0.33 ml of 50% acetic acid and 16 μl of 0.1N HCl. After 10 minutes at RT, the mixture is decolourised by the addition of 40 μl of 1M aqueous ascorbic acid solution and filtered through Sephadex ®1G-25 in 50% acetic acid. The eluate is concentrated in vacuo to approximately 1 ml and subjected to a HPLC purification as described below.

CGRP II of the formula III is obtained.

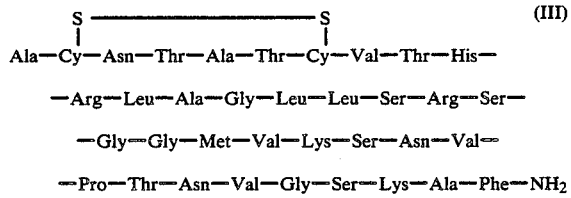

The starting material is obtained in the following manner: Stage 1.1: 30.0 g of chloromethylpolystyrene (20.1 mmol of Cl) are introduced together with 6.1 g (40.2 mmol) of p-hydroxymethylbenzoic acid into 150 ml of degassed dimethylformamide and, over a period of 3 minutes, 6.0 ml (40.2 mmol) of 1,8-diazabicyclo(5,4,0)- undec-7-ene(1,5,5) are added. The RM is stirred for 20 hours at 50°. The resulting resin is filtered off with suction and washed in each case three times with 150 ml each of dimethylformamide, dimethylformamide/water (9:1), methanol, methylene chloride and methanol. The resin is dried under a HV until the weight is constant, whereupon hydroxybenzyl-p-carbonyloxymethylconstant, polystyrene synthetic resin is obtained.

Stage 1.2: 1.1 g (4 mmol) of Boc-Phe and 3.0 g (approx. 2 mmol) of the resin obtained in accordance with Stage 1.1 are suspended in 20 ml of methylene chloride and 1.5 ml of dimethylformamide at RT while stirring gently for approximately 5 minutes. The mixture is cooled to 0°–5° and 865 mg (4.2 mmol) of dicyclohexylcarbodiimide in 1.8 ml of methylene chloride are added in three portions within a period of 5 minutes. After a further 5 minutes, 24 mg (0.2 mmol) of - dimethylaminopyridine and, after 10 minutes, 220 μl of N-methylmorpholine (2 mmol) in 1 ml of methylene chloride are added. The mixture is maintained for one hour at 0° and then for 20 hours at RT. The resin is filtered off and washed in each case 5 times with approximately 50 ml each of methylene chloride, dimethylformamide, methanol, methylene chloride and methanol. After drying under a HV it has a weight of 3.34 g. In order to block unreacted hydroxy groups, the resin is suspended in 20 ml of methylene chloride, 1 ml of pyridine is added and, after cooling in an ice-bath, 1 ml of benzoyl chloride is added thereto. After 15 minutes at 0° and 1 hour at RT, the resin is filtered off with suction and washed in succession, in each case twice, with 50 ml each of methylene chloride, dimethylformamide, methanol, methylene chloride and methanol. The resin is dried under a HV until the weight is constant. The amino acid charge is calculated from the N content as being 0.35 mmol/g.

Stage 1.3: 1.0 g of Boc-Phe resin (0.35 mmol) is subjected in a semi-automatic peptide synthesis machine to the following operations (all washing operations carried out with approximately 20 ml in each case) in order to remove the Boc group, couple on the second amino acid Boc-Ala and remove that Boc group:
x 1×1.0 min. isopropanol,
3×0.5 min. ethylene dichloride,
3×5.0 min., 1×15 min. trifluoroacetic acid chloride to remove the Boc group,
3×0.5 min. ethylene dichloride,
3×2.0 min. isopropanol,
2×0.5 min. ethylene dichloride,
2×0.5 min. dimethylacetamide, degassed,
3×2.0 min. 2% diisopropylethylamine in dimethylacetamide,
2×0.5 min. ethylene dichloride,
3×0.5 min. dimethylacetamide, distilled,
1×120 min. coupling: 1.5 mmol of Boc-Ala, 221 mg (1.5 mmol) of hydroxybenzotriazole, 320 mg (1.6 mmol) of dicyclohexylcarbodiimide in 0.32 ml of ethylene dichloride and 3.5 ml of dimethylacetamide: 20 min. at RT, 100 min. at 45°,
1×2.0 min. 10 ml of acetic anhydride/pyridine/dimethylacetamide (10:10:80, v/v) to block unreacted amino groups,
1×0.5 min. dimethylacetamide, degassed,
1×1.0 min. isopropanol,
2×0.5 min. ethylene dichloride and
2×0.5 min. dimethylacetamide, degassed,
1×1.0 min. isopropanol,
3×0.5 min. ethylene dichloride,
3×5.0 min., 1×15 min. trifluoroacetic acid/ethylene chloride to remove the Boc group,
3×0.5 min. ethylene dichloride,
1×2.0 min. isopropanol,
2×2.0 min. ethylene dichloride,
2×0.5 min. dimethylacetamide, degassed,
3×2.0 min. 2% diisopropylethylamine in dimethylacetamide,
2×0.5 min. ethylene dichloride,
3×0.5 min. dimethylacetamide, distilled.

Stage 1.4: In the above-mentioned peptide synthesis machine, the following amino acids are condensed in succession onto the product obtained in accordance with stage 1.3:

Fmoc-Lys(Boc), Fmoc-Ser(tBu), Fmoc-Gly, Fmoc-Val, Fmoc-Asn, Fmoc-Thr(tBu), Fmoc-Pro, Fmoc-Val, Fmoc-Phe, Fmoc-Asn, Fmoc-Ser(tBu), Fmoc-Lys(Boc), Fmoc-Val, Fmoc-Met, Fmoc-Gly, Fmoc-Gly, Fmoc-Ser(tBu), Fmoc-Arg(Mtr), Fmoc-Ser(tBu), Fmoc-Leu, Fmoc-Leu, Fmoc-Gly, Fmoc-Ala, Fmoc-Leu, Fmoc-Arg(Mtr), Fmoc-His(Fmoc), Fmoc-Thr(tBu), Fmoc-Val, Fmoc-Cys(Acm), Fmoc-Thr(tBu), Fmoc-Ala, Fmoc-Thr(tBu), Fmoc-Asn, Fmoc-Cys(Acm) and Boc-Ala.

For this, the following cycle of operations is carried out in each case, the Fmoc protecting group being removed from the preceding amino acid in each case:
1×1.0 min. isopropanol,
2×0.5 min. ethylene dichloride,
1×0.5 min. dimethylacetamide, degassed,
1×1.0 min. isopropanol,
3×0.5 min. dimethylacetamide, degassed,
4×2.0 min. 20% (vol.) piperidine in dimethylacetamide,
2×0.5 min. dimethylacetamide, degassed,
2×1.0 min. water/peroxide-free dioxan (1:2 v/v),
2×0.5 min. dimethylacetamide, degassed,
2×0.5 min. ethylene dichloride,
3×0.5 min. dimethylacetamide, distilled,
81×120 min. coupling: 1.5 mmol of Fmoc-amino acid or, at the end, Boc-Ala, 221 mg (1.5 mmol) of hydroxybenzotriazole, 320 mg (1.6 mmol) of dicyclohexylcarbodiimide in 0.32 ml of ethylene dichloride and 3.5 ml of dimethylacetamide: 20 min. at RT, 100 min. at 45°,
1×2.0 min. 10 ml of acetic anhydride/pyridine/dimethylacetamide (10:10:80, v/v),
1×0.5 min. dimethylacetamide, degassed, 1×1.0 min. isopropanol,
3×0.5 min. ethylene dichloride and
2×0.5 min. dimethylacetamide, degassed.

The completeness of the coupling reaction is tested qualitatively by detection of unreacted amino groups with ninhydrin (Kaiser test). If the test is positive, the resin is washed with ethylene chloride and a subsequent coupling with 1.5 mmol of amino acid derivative and 1.6 mmol of dicyclohexylcarbodiimide in 3.8 ml of ethylene dichloride/trifluoroethanol (75:25) is carried out for 120 min. at RT. After the last coupling, the resin is washed exhaustively with dimethylacetamide, ethylene dichloride and isopropanol and dried under a HV.

Stage 1.5: In order to remove the tBu and Boc protecting groups, the product obtained in accordance with Stage 1.4 is treated in the following manner at RT (30 ml in each case):
2×2 min. methylene chloride,
1×5 min. trifluoroacetic acid/methylene chloride/1,2-ethanedithiol/m-cresol (50:43:2:5),
1×30 min. trifluoroacetic acid/methylene chloride/1,2-ethanedithiol/m-cresol (50:43:2:5),
1×60 min. trifluoroacetic acid/methylene chloride/1,2-ethanedithiol/m-cresol (50:43:2:5),
2×2 min. methylene chloride and
2×2 min. methanol.

Stage 1.6: For the purpose of detaching the peptide from the resin and for the purpose of amidating the terminal carboxy group, the product obtained in accordance with stage 1.5, after being dried under HV, is suspended in 30 ml of dimethylformamide. At −70°, approximately 10 ml of ammonia are condensed in. Excess ammonia is evaporated off at 0° and the mixture is stirred in a pressure vessel for 20 hours at RT. The resin is filtered off, washed twice with water (20 ml each time), 3 times with methanol/water (1:1) and 10 times with trifluoroethanol/water (1:1) and the filtrate is concentrated by evaporation. The residue is dissolved in 30 ml of acetic acid/water (9:1) and lyophilised.

Stage 1.7: In order to remove the Mtr groups, the lyophilisate obtained in accordance with Stage 1.6 is dissolved in 20 ml of trifluoroacetic acid/1,2-ethanedithiol (99:1). 1.5 ml of m-cresol are added and the mixture is maintained at 50° for 2 hours. The crude di-Acm peptide is precipitated by the addition of 100 ml of diethyl ether, filtered off and washed with diethyl ether. The product is dissolved in 25 ml of acetic acid/water (1:1), the turbidity is filtered off and the filtrate is used for analytical separation in HPLC.

The HPLC is carried out under the following conditions:
column: Nucleosil 10 μm $C_{18}$ (Macherey Nagel, Düren, Federal Republic of Germany), 200×4.8 mm, linear gradient 0%–90% B, 60 min. A: 0.1% trifluoroacetic acid in water, B: 0.1% trifluoroacetic acid in acetonitrile.

The material corresponding to the main peak is collected and its identity with the desired product is confirmed by FAB-MS (mass peak: 3937.6).

Micropreparative separation: 100 mg of the crude product are separated over a 250×21 mm column. The collected fractions are concentrated by evaporation in vacuo. The residue is dissolved in 2 ml of water, filtered and lyophilised.

EXAMPLE 2

*Escherichia coli* clones containing plasmids with the DNA insert of the formula XIV d(GAATTCATGGCTTGCAACACCGCTACCTGCGTTACCCACCGTCTGGCT        (XIV)

d(CTTAAGTACCGAACGTTGTGGCGATGGACGCAATGGGTGGCAGACCGA

GGTCTGCTGTCTCGTTCTGGTGGTATGGTTAAATCTAACTTCGTTCCGACC

CCAGACGACAGAGCAAGACCACCATACCAATTTAGATTGAAGCAAGGCTGG

AACGTTGGTTCTAAAGCTTTCTACTAGGATCC)

TTGCAACCAAGATTTCGAAAGATGATCCTAGG)

are cultivated in 5 ml of L medium overnight (16 hours) at 37° C. and 250 rev/min. The composition of L medium is as follows:

| | |
|---|---|
| Bacto tryptone | 10 g |
| Bacto yeast extract | 5 g |
| NaCl | 5 g |
| glucose | 5 g |
| ampicillin | 0.1 g |

1 ml of this overnight culture is transferred the next day into 25 ml of M9 medium. The composition of M9 medium is as follows:

| | |
|---|---|
| $Na_2HPO_4.7H_2O$ | 13.25 g |
| $KH_2PO_4$ | 3.0 g |
| NaCl | 0.5 g |
| $NH_4Cl$ | 1.0 g |
| $CaCl_2.2H_2O$ | 0.015 g |
| $MgSO_4.7H_2O$ | 0.25 g |
| casamino acids | 2.5 g |
| vitamin $B_1$ | 0.0099 g |
| glucose | 5.0 g |
| ampicillin | 0.1 g |

Cultivation is carried out at 37° C. and 250 rev/min until the bacterial suspension has reached an optical density ($OD^{623}$) of approximately 0.9–1.0. Subsequently, the cells are harvested (5 ml of the growing culture) and the bacteria are resuspended in 0.5 ml of a solution of 50 mM tris·HCl (pH 8) and 30 mM NaCl. The suspension is then standardised against 1 mg/ml lysozyme (Boehringer) and placed in ice for 30 minutes. By alternately freezing the suspension in liquid nitrogen and thawing at 37° C., the bacteria are disintegrated. This procedure is repeated 5 times, and the mixture is subsequently centrifuged for 30 minutes at 16,000 rev/min and 4° C. The supernatants are examined for content of CGRP IIa by means of HPLC or by means of antibodies.

Alternatively, the above-mentioned bacterial suspension is worked up in the following manner:

The cells are separated from the culture solution by means of centrifugation at more than 8000 rev/min and subsequently disintegrated mechanically in a Dyno-Mill mill or enzymatically in a lysis buffer (pH 8) by means of lysozyme.

The following steps are then carried out one after the other:

1. pH-precipitation of the bacterial proteins by means of acetic acid (final concentration 1%, pH 4.0), CGRP II remaining in the supernatant and the sediment being separated off.
2. In a batch process, the crude peptide is adsorbed on an ion-exchanger column (CH 52, Whatman) and eluted by means of a salt gradient of from 10 mM ammonium acetate (pH 4.5) to 300 mM (pH 6.5). The main component is desalinated by repeated lyophilisation from distilled water or by diafiltration. 3. The product is purified by means of multiplicative partitioning according to Craig in a two-phase system of 0.1% acetic acid/n-butanol (1:1) (200 transfers). The solvent is removed in a rotary evaporator and the collected fractions are lyophilised. 4. Any residual proteins and low molecular weight constituents are separated off by gel-filtration chromatography over Sephadex®G 50 (Pharmacia), elution being carried out with 2% acetic acid, 1% β-mercaptoethanol, or by means of reverse-phase HPLC on the preparative apparatus of Waters (LC-Prep 500) over a Nucleosil -C 18 column (Dydac 300 Å, 15–20 μm) by means of a solvent gradient.

CGRP IIa of the formula XV is obtained.

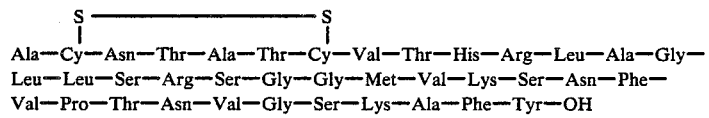

(XV)

Ala—Cy—Asn—Thr—Ala—Thr—Cy—Val—Thr—His—Arg—Leu—Ala—Gly—
Leu—Leu—Ser—Arg—Ser—Gly—Gly—Met—Val—Lys—Ser—Asn—Phe—
Val—Pro—Thr—Asn—Val—Gly—Ser—Lys—Ala—Phe—Tyr—OH

The E. coli clones used as starting material are obtained in the following manner:

Staqe 2.1:

750 mg of succinic anhydride and 910 mg of 4-dimethylaminopyridine are added to 3.05 g (5 mmol) of 5'-(4-monomethoxytrityl)-N-isobutyryl-deoxyguanosine in 20 ml of abs. pyridine and the whole is left for 16 hours at room temperature. After concentration of the pyridine solution, the residue is taken up in 200 ml of ethyl acetate, extracted twice by shaking with 200 ml of 0.1M phosphate buffer with the addition of 10 ml of saturated sodium chloride solution each time, washed again with saturated sodium chloride solution, dried, concentrated and hexane is added dropwise. The precipitated product is separated off and triturated twice with diethyl ether, then dissolved in 300 ml of ethyl acetate and extracted by shaking at 0° with 180 ml of 0.1M potassium bisulphate of pH 2.5. After washing twice with water, the ethyl acetate solution is dried with sodium sulphate, filtered, 0.5 ml of pyridine is added thereto, and the whole is concentrated and diluted dropwise with hexane. The precipitated succinic acid derivative is filtered off.

1.15 g of this compound are dissolved together with 190 mg of N-hydroxysuccinimide in 4 ml of ethyl acetate and 2 ml of dimethylformamide and, at 0°, 370 mg of N,N'-dicyclohexylcarbodiimide are added. After standing overnight in a refrigerator, the precipitated N,N'-dicyclohexylurea is filtered off, the filtrate is diluted with ethyl acetate, extracted with cold 0.1M sodium bicarbonate and water, dried and concentrated to dryness by evaporation in vacuo. The residue is chromatographed over silica gel using ethyl acetate. TLC: $R_f$ 0.55 in dichloromethane/methanol (9:1).

100 mg of this N-succinimidoylsuccinic acid ester are stirred with 1 g of aminomethylpolystyrene (amine content 110 μmol/g) in 2 ml of dichloromethane and 4 ml of dimethylformamide for 20 hours. The polymer resin is filtered off and washed with dimethylformamide, methanol, dichloromethane and methanol. After drying, the unreacted amino groups are acetylated by stirring the resin in 6 ml of pyridine with 1 ml of acetic anhydride and 100 mg of 4-dimethylaminopyridine for 30 minutes. The resulting polymer resin, in which 5'-(4-monomethoxytrityl)-N-isobutyryl-deoxyguanosyl-3'-O-succinyl radicals are linked to the amino groups of the aminomethylpolystyrene, is washed with dichloromethane, dimethylformamide, methanol and dichloromethane and dried until the weight is constant. Spectroscopic methoxytrityl analysis shows a charge of 32 μmol/g.

Stage 2.2:

7.73 g (15 mmol) of 5'-(4-monomethoxytrityl)thymidine are twice concentrated by evaporation with abs. pyridine. The residue is dissolved in 20 ml of abs. tetrahydrofuran and the solution is added dropwise, while stirring and with the exclusion of moisture, to 80 ml of a 0.2M solution of 2 -chlorophenyl-di-(1-benzotriazolyl)-phosphate in tetrahydrofuran, and the reaction mixture is stirred for 1 hour at room temperature. The resulting solution of 2-chlorophenyl-1-benzotriazolyl-5'-(4-monomethoxytrityl)-thymidine 3'-phosphate is divided into three portions.

(α) Hydrolysis to triethylammonium 2-chlorophenyl-5'(4-monomethoxytrityl)-thymidine 3'-phosphate:

To a third of the above solution of 2-chlorophenyl-1-benzotriazolyl-5'-(4-monomethoxytrityl)thymidine 3'-phosphate there are added, while cooling, 100 ml of 0.5 M triethylammonium bicarbonate. After 15 minutes, extraction is carried out with dichloromethane. The dichloromethane solution is washed with water and concentrated, and petroleum ether is added dropwise thereto. The resulting precipitate is filtered off with suction, washed with diethyl ether/petroleum ether (1:1) and dried in vacuo. TLC: $R_f$ 0.35 in dichloromethane/methanol/water (75:22:3).

(β) Esterification to 2-cyanoethyl-2-chlorophenyl-5'-(4-monomethoxytrityl)-thymidine 3'-phosphate and removal of the 4-monomethoxytrityl protecting group:

To a third of the solution of 2-chlorophenyl-1-benzotriazolyl-5'-(4-monomethoxytrityl)-thymidine 3'-phosphate there are added 1.3 ml of 2-cyanoethanol and 2 ml of pyridine. The mixture is left overnight at room temperature. The solvents are distilled off in vacuo and the residue is dissolved in ethyl acetate and extracted several times by shaking with 0.1M phosphate buffer pH 7 and water. The organic phase is dried, concentrated and added dropwise to hexane. The precipitate is filtered off, dissolved in 50 ml of dichloromethane/methanol 7:3 and, at 0°, a solution of 3.8 g of p-toluenesulphonic acid monohydrate in 75 ml of dichloromethane/methanol 7:3 is added thereto. After 2 hours, the reaction solution is diluted with dichloromethane and extracted by shaking with a cold sodium bicarbonate solution. The organic phase is concentrated and hexane is added thereto. The precipitated 2-cyanoethyl-2-chlorophenyl-thymidine 3'-phosphate is chromatographed over silica gel using dichloromethane/methanol (96:4). TLC: $R_f$ 0.45 in dichloromethane/methanol (9:1).

(γ) Condensation to 5'-(4-methoxytrityl)-3'-cyanoethyl)bisthymidine dinucleotide:

trinucleotide is purified by chromatography over silica gel; $R_f=0.45$ in dichloromethane/methanol (9:1).

Stage 2.5:

In a manner analogous to that of Stages 2.2, 2.3 and 2.4, the following protected trinucleotides of the general formula XVI are manufactured:

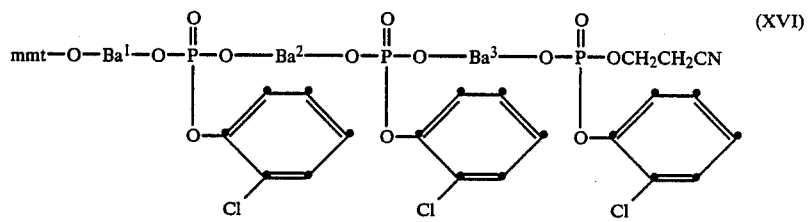

2.2 g of 2-cyanoethyl-2-chlorophenyl-thymidine 3'-phosphate are dehydrated by twice concentrating by evaporation with abs. pyridine, are dissolved in 20 ml of abs. tetrahydrofuran and added to the remaining third of the solution of 2-chlorophenyl-1-benzotriazolyl5'-(4-monomethoxytrityl)-thymidine 3'-phosphate. After 18 hours at room temperature, there are added to the reaction solution, while cooling with ice, 10 ml of water and 200 ml of ethyl acetate. The organic phase is washed several times with sodium bicarbonate and water, dried over sodium sulphate and concentrated to a small volume. The dinucleotide which is protected in the phosphate moiety and at the 5'- and 3'-ends is precipitated by being added dropwise to diethyl ether/hexane 1:1; $R_f=0.48$ in dichloromethane/methanol (9:1).

Stage 2.3:

9.20 g (15 mmol) of 5'-(4-monomethoxytrityl)-N-isobutyryl-deoxyguanosine are twice concentrated by evaporation with abs. pyridine. The residue is dissolved in 20 ml of abs. tetrahydrofuran and the solution is added dropwise, while stirring and with the exclusion of moisture, to 75 ml of a 0.2M solution of 2-chlorophenyl-di-(1-benzotriazolyl)-phosphate in tetrahydrofuran and the reaction mixture is stirred for 1 hour at room temperature. The resulting solution of 2-chlorophenyl-1-benzotriazolyl-5'-(4-monomethoxytrityl)-N-isobutyryl-guanosyl 3'-phosphate is further processed in Stage 2.4.

Stage 2.4:

1.17 g (1 mmol) of the fully protected dinucleotide described above are dissolved in 30 ml of dichloromethane/methanol (7:3) and, while cooling with ice, a solution of 1.9 g of p-toluenesulphonic acid monohydrate in 20 ml of dichloromethane/methanol (7:3) is added thereto. After 2 hours, ice-cold sodium bicarbonate solution is added and extraction is carried out with dichloromethane. The organic phase is dried, concentrated and introduced dropwise into hexane. The precipitated crude dinucleotide having a free 5'-hydroxy group is chromatographed over silica gel with a gradient of 2%–8% methanol in dichloromethane. $R_f=0.33$ in dichloromethane/methanol (9:1).

900 mg of this 5'-hydroxy-dinucleotide are twice concentrated by evaporation with pyridine, then dissolved in 5 ml of abs. tetrahydrofuran, and 10 ml of the solution obtained in Stage 2.3 are added thereto. After 2 hours, 2 ml of ice-cold water are added and, after a further hour, extraction is carried out with dichloromethane. The organic phase is washed with saturated sodium bicarbonate solution and water, dried and concentrated, and ether is added thereto. The precipitated in which $Ba^1$, $Ba^2$ and $Ba^3$ each represents, independently of one another, the bivalent radical of one of the following nucleosides:

N-benzoyl-deoxyadenosine (A')
N-benzoyl-deoxycytidine (C')
N-isobutyryl-deoxyguanosine (G') or
thymidine (T).

| trinucleotide | | | |
|---|---|---|---|
| $Ba^1$ | $Ba^2$ | $Ba^3$ | $R_f(I)$ |
| T | T | C' | 0.55 |
| T | C' | T | 0.46 |
| T | C' | G' | 0.45 |
| T | A' | C' | 0.56 |
| T | A' | A' | 0.53 |
| T | A' | G' | 0.60 |
| T | G' | C' | 0.44 |
| T | G' | G' | 0.43 |
| C' | T | T | 0.53 |
| C' | T | G' | 0.46 |
| C' | C' | T | 0.45 |
| C' | C' | A' | 0.51 |
| C' | A' | C' | 0.51 |
| C' | A' | A' | 0.52 |
| C' | A' | G' | 0.44 |
| C' | G' | T | 0.49 |
| C' | G' | A' | 0.38 |
| A' | T | T | 0.55 |
| A' | T | G' | 0.48 |
| A' | C' | C' | 0.48 |
| A' | A' | C' | 0.46 |
| A' | A' | G' | 0.51 |
| A' | G' | T | 0.45 |
| A' | G' | A' | 0.49 |
| G' | C' | T | 0.55 |
| G' | A' | T | 0.44 |
| G' | A' | A' | 0.50 |
| G' | G' | T | 0.46 |

Stage 2.6:

Each of the trinucleotides described in Stages 2.4 and 2.5 is treated in the following manner in order to remove the 2-cyanoethyl protecting group: 10 μmol of trinucleotide are dissolved, with the exclusion of moisture, in 60 μl of pyridine/acetonitrile/triethylamine (1:1:1). After 1 hour at room temperature, 0.7 ml of peroxide-free diethyl ether is added dropwise and the precipitate is centrifuged off. The crude triethylammonium salt is dissolved in 50 μl of pyridine and again precipitated with 0.5 ml of diethyl ether, centrifuged off and dried for 15 hours under a high vacuum.

Stage 2.7:

Coupling of the partially protected trinucleotides obtained in accordance with Stage 2.6 to the protected guanosine-polystyrene resin obtained in accordance with Stage 2.1 is carried out in the following manner:

All of the operations are carried out with the exclusion of moisture in a reaction vessel of 150 μl capacity with microprocessor-controlled solvent and reagent addition 15 mg (0.48 μmol) of the guanosinepolystyrene resin (Stage 2.1) are placed in the reaction vessel and subjected to the following operations:

1. methylene chloride, 2 ml/min., 4 min.
2. methylene chloride/isopropanol (85:15), 2 ml/min., 2 min.
3. zinc bromide 1M and 1,2,4-triazole 0.02M in methylene chloride/isopropanol (85:15), 2 ml/min., 2–3.5 min.
4. methylene chloride/isopropanol (85:15), 2 ml/min., 4 min.
5. triethylammonium acetate, 0.5M in DMF, 2 ml/min., 5 min.
6. molecular sieve-dried pyridine, 2 ml/min., 3 min.
7. tetrahydrofuran (peroxide-free, molecular sieve-dried), 2 ml/min., 3 min.
8. nitrogen stream, 10 min.
9. injection 10 μmol trinucleotide (see below) and 8.9 mg (30 μmol) 1-mesitylenesulphonyl-3-nitro-1,2,4-triazole (MSNT) dissolved in 150 μl pyridine.
10. 45°, 20 min.
11. pyridine, 2 ml/min., 4 min.
12. acetic anhydride 5% and 4-dimethylaminopyridine 2.5% in pyridine, 2 ml/min., 4 min.
13. pyridine, 2 ml/min., 4 min.
14. pyridine/isopropanol (1:1), 2 ml/min., 3 min.

All 14 operations are repeated 24 times, the following deoxytrinucleotides in the form of their triethylammonium salts (see Stage 2.6) being used in succession in the 9th operation: d(A'A'C', C'A'G', C'A'C', TA'C', C'C'A', TA'A', A'TT, TA'G', A'G'T, C'G'A', G'A'A', TC'G', TG'G', C'G'T, C'A'A', A'A'C', TA'G', C'TT, A'A'G', A'G'A', A'G'T, C'C'T, C'A'T and G'TC').

The mean coupling yield is 97%. The end product has the following structure, the 2-chlorophenyl protecting groups still being additionally present therein: d(mmt-G'TC'C'A'TC'C'TA'G'T'A'G'A'A'A'G'-C'TTTA'G'A'A'C'C'A'A'C'G'TTG'G'TC'G'G-'A'A'C'G'A'A'G'TTA'G'A'TTTA'A'C'C'A'TA'C'-C'A'C'C'A'G'A'A'C'C'G')-polystyrene synthetic resin.

Stage 2.8:

The polydeoxynucleotide-polystyrene synthetic resin obtained in accordance with Stage 2.7 is treated in the following manner for the purpose of removing the polynucleotide from the carrier and for the purpose of removing the protecting groups:

35.0 mg (approximately 0.35 μl mol) of polydeoxynucleotide synthetic resin 64/73 are maintained together with 66 mg (0.40 mmol) of o-nitrobenzaldoxime and 50 μl (0.40 mmol) of 1,1,3,3-tetramethylguanidine in 400 μl of 95% pyridine for 3 hours at 50° and for 12 hours at room temperature. After blowing off the pyridine with nitrogen, 1.6 ml of aqueous ammonia (33%) are added to the residue and the whole is maintained for 24 hours at 50° C. in a closed vessel.

The liquid phase, separated off, is freed of ammonia in vacuo and washed 3 times with 3 ml of peroxide-free diethyl ether each time. After separating off the low molecular weight constituents over a Biogel P6 column (100–200 mesh, 3×66 cm, 0.01M trimethylammonium bicarbonate pH 7.5, 1.5 ml/min.), 250 ODs (260 nm) of polydeoxynucleotide are isolated.

A total of 60 ODs are separated over a HPLC column (PRP-1/Hamilton, 250×4.6 mm). Gradient (solution A: 0.05M triethylammonium acetate pH 7.0; solution B: solution A/acetonitrile 1:1) from 30% B in A to 60% B in A in 20 min. at 50° C. and 2 ml/min. The lipophilic main peak (retention time approximately 14 min.) is collected, concentrated over a DE52-cellulose (Whatman) column, eluted, and precipitated with ethanol. In order to remove the 4-methoxytrityl protecting group, the precipitate is dissolved in 50 μl of acetic acid/H$_2$O (4:1) and maintained for 45 min. at room temperature. The reaction product is lyophilised, precipitated with ethanol and, for purification, separated electrophoretically over an 8% polyacrylamide gel (7M urea). The band corresponding to the expected polydeoxynucleotide size is cut out and the product is electroeluted, concentrated over DE52-cellulose and the polydeoxynucleotide 64/73 of the structure d(GTCCATC-CTAGTAGAAAGCTTTAGAAC-CAACGTTGGTCG GAACGAAGTTAGATT-TAACCATACCACCAGAACG) is precipitated with ethanol.

Stage 2.9:

Analogously to Stages 2.7 and 2.8, there is obtained the polydeoxynucleotide (1/73) d(CTGGAATT-CATGGCTTGCAACACCGCTACCTGCGT-TACCCACCGTCTGGCTGGT CTGCTGTCTCGTTCTGGTG).

Stage 2.10:

The polynucleotides (64/73 and 1/73 complementary) obtained in accordance with Stages 2.8 and 2.9 are radioactively phosphorylated at the 5'-ends with [γ-$^{32}$P]ATP and T$_4$ polynucleotide kinase (Boehringer, Federal Republic of Germany) as described in Molecular Cloning, A Laboratory Manual (published by T. Maniatis et al.), Cold Spring Harbor Lab. 1982, page 125.

Stage 2.11:

For polymerisation of the kinased polynucleotides obtained in accordance with Stage 2.10 to form the duplex 50 pmol each of kinased fragment 1/73 and kinased fragment 64/73 are dissolved in 24 μl of water, the solution is heated for 3 min. at 90° C. and cooled within a period of 5 min. to 12° C. After the addition of 4 μl of endo-R buffer (0.1 molar tris·HCl pH 7.5, 66 mM MgCl$_2$, 66 mM μ-mercaptoethanol, 0.6M NaCl), 10 μl of deoxynucleoside triphosphate mixture (dATP, dCTP, dGTP, TTP, each 2·10$^{-3}$ molar, adjusted to pH 7.0 with NH$_3$) and 2 μl (10 units) of DNA polymerase I, Klenow Fragment (Boehringer), incubation is carried out for 30 min. at 12° C. The reaction is stopped by heating at 90° C. for 3 minutes and the mixture is stored at −80° C. until further processed.

The resulting DNA-duplex has the following structure d(CTGGAATTCATGGCTTGCAACACCGCTACCTGCGTTACCCACCGTCTGGCT
d(GACCTTAAGTACCGAACGTTGTGGCGATGGACGCAATGGGTGGCAGACCGA
GGTCTGCTGTCTCGTTCTGGTGGTATGGTTAAATCTAACTTCGTTCCGACC
CCAGACGACAGAGCAAGACCACCATACCAATTTAGATTGAAGCAAGGCTGG
AACGTTGGTTCTAAAGCTTTCTACTAGGATCCTG)

-continued

TTGCAACCAAGATTTCGAAAGATGATCCTAGGAC)

This duplex is referred to hereinafter as "$F_o$".

Stage 2.12:

10 μg of plasmid pBRH$_{trp}$ [German Offenlegungsschrift 3 111 405 (Genentech)] are cleaved with 50 units of EcoRI (Biolabs) for 60 min. at 37° C., and, after phenol extraction, the digestion mixture is fractionated through a saccharose density gradient (5%–23%) in 50 mM tris·HCl (pH 8.0), 1 mM EDTA in a TST41 (Kontron AG) rotor. Centrifugation lasts 14 hours at 40,000 rev/min and 15° C. 0.3 ml fractions are collected with an ISCO gradient collector at 1 ml/min. The fractions containing the smaller fragment are combined, the solution is standardised against TNE and precipitated with 2 volumes of ethanol at −20° C. After centrifugation in an Eppendorf centrifuge, the DNA is dissolved in 100 μl of 10 mM tris·HCl pH 7.5, 0.5 mM EDTA. 5 μg of this DNA fragment are cleaved with 5 units of BglII (Biolabs) for 60 min. at 37° C. The reaction mixture is extracted with phenol and chloroform and the DNA is incubated with 2 volumes of ethanol at −80° C. for 10 min., and the DNA is collected by centrifugation and again dissolved in 50 μl of 50 mM tris·HCl (pH 8.0). 2 μl of this solution are taken (0.2 μg of DNA) and incubated at a DNA concentration of 10 ng/μl in 50 mM tris·HCl (pH 8.0) with 1 unit of intestinal alkaline calf phosphatase (Boehringer) for 30 min. at 37° C. The enzyme is deactivated by heating the solution for 60 min. at 65° C. 0.04 μg of DNA is taken and radioactively phosphorylated 5′-terminally by incubation with 10 μCi of [γ-$^{32}$P]-ATP (>5000 Ci/mmol, Amersham) and 5 units of T$_4$ polynucleotide kinase (P-L Biochemicals) in 50 mM tris·HCl (pH 9.5), 10 mM MgCl$_2$, and 5 mM DTT in 20 μl reaction volume, for 30 min. at 37° C. The radioactive sample is mixed with the unlabelled sample (see above) and the DNA fragments are fractionated through a 5%–23% saccharose density gradient in 50 mM tris·HCl (pH 8.0), 1 mM EDTA in a TST60 rotor. The centrifugation is carried out for 5 hours at 60,000 rev/min and 15° C. 0.2 ml fractions are collected. The radioactivity of each fraction is determined by measuring the Cerencov radiation and the fragments are thereby identified. The desired fractions which contain the small DNA fragment are combined, the DNA is precipitated with 2 volumes of ethanol and, after centrifugation, again dissolved in 20 μl of 10 mM tris·HCl pH 7.5, 0.5 mM EDTA.

The $^{32}$P-labelled EcoRI-BglII DNA fragment is partially cleaved with 0.2 units of TaqI (Biolabs) in 50 μl volume for 10 min. at 37° C. The reaction mixture is standardised against 0.2% SDS, 10% glycerine, 10 mM EDTA, 0.05% bromophenol blue and the DNA fragments are separated on a 6% polyacrylamide gel in tris-borate-EDTA [A. C. Peacock et al., Biochemistry 6, 1818 (1967)]. The band containing the desired EcoRI-TaqI fragment (the largest partial fragment) is identified on the autoradiograph. This fragment (L, see FIG. 1) is extracted from the gel and purified [W. Müller et al., J. Mol. Biol. 124, 343 (1978)] and dissolved in 10 μl of 10 mM tris·HCl pH 7.5, 1 mM EDTA.

pBR322 that has been cleaved with ClaI and EcoRI is used as the acceptor plasmid: 2 μg of pBR322 are digested with 4 units of ClaI (Biolabs) in 20 μl reaction volume for 60 min. at 37° C. The protein is extracted with phenol and the DNA is subsequently precipitated with 2 volumes of ethanol at −80° C. for 10 min. The DNA is collected by centrifugation and then digested with 10 units of EcoRI (Biolabs) for 30 min. at 3720 C. in 20 μl reaction volume. Subsequently, 2 volumes 37° C of 0.1M tris·HCl (pH 8.7) are added to the solution and the whole is incubated with 1 unit of alkaline calf phosphatase (Boehringer) for 30 min. at 37° C. The phosphatase is subsequently deactivated by incubation at 65° C. for 60 min.

100 ng of the acceptor plasmid are incubated with 5 μl of fragment L-DNA in 15 μl reaction volume in 10 mM MgCl$_2$, 20 mM tris·HCl (pH 7.8), 10 mM DTT, 0.5 mM ATP with 30 units per μl of reaction volume of T$_4$ DNA ligase (Biolabs) for 2 hours.

5 μl of this solution are added to a mixture containing 150 μl of E. coli HB101 cells (14) that have been treated with calcium chloride, in 10 mM MgCl$_2$, 10 mM CaCl$_2$ and 10 mM tris·HCl (pH 7.5) in a total volume of 200 μl. The mixture is cooled in ice for 20 min., heated at 42° C. for 1 min. and incubated for 10 min. at 20° C. 1 ml of tryptone medium [tryptone medium contains 10 g of Bacto-tryptone (Difco); 1 g of yeast extract (Difco); 1 g of glucose; 8 g of NaCl and 294 mg of CaCl$_2$.2H$_2$O in 1 liter of distilled water] is added and the mixture is incubated for 30 min. at 37° C. while shaking at 300 rev/min. The mixture is plated onto two agar plates (McConkey Agar, Difco; 0.6 ml/plate) supplemented by 50 μg/ml ampicillin (Sigma). The plates are incubated for from 12 to 17 hours at 37° C.

The plasmid DNA of 10 different colonies is isolated as follows:

For inoculation of 10 ml of tryptone medium supplemented by 50 μg/ml ampicillin, as above, the colonies are used in a 25 ml Erlenmeyer flask. The cultures are shaken for from 15 to 18 hours at 37° C. and 300 rev/min. The cells are harvested by centrifugation (Sorval, HS-4 rotor, 10 min. at 4000 rev/min, 4° C.). Approximately 0.1 g of cells is obtained and these are resuspended in 1 ml of 50 mM tris·HCl (pH 8.0). 0.25 ml of lysozyme solution [10 mg/ml in 50 mM tris·HCl (pH 8.0); lysozyme is marketed by Sigma] is added and, after 10 minutes' incubation at 0° C., 0.15 ml of 0.5M EDTA (pH 7.5) is added. After a further 10 min. at 0° C., 60 μl of 2% Triton X-100 (Merck) are added. After 30 min. at 0° C., the sample is centrifuged for 30 min. at 15,000 rev/min and 4° C. in a Sorval SA-600 rotor. The supernatant is deproteinated with 1 vol. of phenol (saturated in TNE). The phases are separated by centrifugation (Sorval HB-4 rotor) for 10 min. at 5000 rev/min and 4° C. The upper phase is extracted twice with 1 vol. of chloroform. Pancreatic RNAse A (Sigma; 10 mg/ml in TNE preheated for 10 min. at 85° C.)

is added until a final concentration of 25 μg/ml is reached and the mixture is incubated for 40 min. at 37° C. The solution is then standardised against 1M NaCl and 10% polyethylene glycol 6000 (Fluka, treated in an autoclave for 20 min. at 120° C.) and incubated for 2 hours at −10° C. The precipitate is collected in a Sorval HB-4 rotor (20 min. at 10,000 rev/min, 0° C.) and again dissolved in 100 μl of TNE. The DNA solution is extracted with 1 vol. of phenol and the DNA is precipitated with 2 vol. of ethanol for 10 min. at −80° C. The precipitate is collected by centrifugation in an Eppendorf centrifuge and the DNA is again dissolved in 20 μl of 10 mM tris·HCl (pH 7.5) and 0.5 mM EDTA. From 8 to 10 μg of plasmid DNA are obtained from a 10 ml culture.

The plasmid DNAs are analysed after digestion with the following restriction enzymes:

0.5 μg in each case of plasmid DNA is cleaved with HpaI (Biolabs) and also with HpaI (Biolabs) and EcoRI (Biolabs) with ClaI (Biolabs) according to standard instructions, as specified by the enzyme manufacturer. The DNAs are fractionated over a 1% agarose gel in 40 mM tris.acetate (pH 7.8), 1 mM EDTA and 0.5 μg/ml ethidium bromide. The desired plasmids contain an HpaI site and yield, after the 3-fold digestion, apart from the large DNA fragment, 2 smaller fragments which are larger than the small EcoRI-ClaI fragment of pBR322. One of these plasmids is designated p159.

Stage 2.13:

2 μg of p159 DNA are digested with 10 units of EcoRI (Biolabs) for 30 min. at 37° C. The DNA is extracted with phenol, precipitated with ethanol and, after centrifugation, dissolved in 10 μl of 10 mM tris.HCl (pH 7.5), 0.5 mM EDTA. The DNA digested with EcoRI is further treated with 5 units of DNA polymerase (Klenow fragment) (Boehringer) in 10 mM MgCl$_2$, 10 mM β-mercaptoethanol, 50 nM NaCl, 0.1 mM dATP (P&L Biochemicals), 0.1 mM dTTP (P&L Biochemicals) for 15 min. at 12° C. The polymerase is subsequently deactivated by incubation at 85° C. for 5 min. The reaction mixture is diluted 10-fold in 20 mM tris.HCl (pH 7.8), 10 mM MgCl$_2$, 10 mM DTT, 0.5 mM ATP (Sigma) and incubated with 30 units of T$_4$ DNA ligase per μl of reaction mixture for 1 hour at 15° C.

50 ng of the DNA are transformed in *E. coli* (as described above) and plated out onto McConkey agar plates supplemented by 50 μg/ml ampicillin.

The plasmid DNA of 10 different colonies is isolated as described above. The plasmid DNAs are analysed by digestion with EcoRI. The desired plasmids are EcoRI-resistant. The analysis is effected as described above. One of the desired plasmids is designated HRi145.

Stage 2.14:

2 μg of pHRi145 DNA are treated with 5 units of ClaI (Boehringer) for 60 min. at 37° C., then deproteinated by means of phenol extraction. The DNA is precipitated with ethanol and then dissolved in 20 μl of 10 mM tris.HCl (pH 7.5), 0.5 mM EDTA. The projecting ends are, as described above, made up with DNA polymerase I (Klenow fragment), except that dATP and dTTP are replaced by dCTP (P&L Biochemical) and dGTP (P&L Biochemicals). The polymerase is deactivated by incubation at 85° C. for 5 min. 2 volumes of 0.1M tris.HCl (pH 8.7) are added to the reaction mixture and the whole is incubated with 0.5 units of calf phosphatase (Boehringer) for 30 min. at 37° C. The reaction mixture is deproteinated by phenol extraction. The DNA is precipitated with ethanol and dissolved in 8 μl of 10 mM tris.HCl (pH 7.5), 0.5 mM EDTA.

A chemically synthesised DNA linker of the formula

5'-GAATTCCATGGTACCATGGAATTC-3' is phosphorylated at the 5'-end by incubating 8 pmol of the linker with 5 μCi of [γ-$^{32}$P]-ATP (5500 Ci.mmol$^{-1}$ Amersham) in 8 μl reaction volume, which contains 0.1 mM rATP (Sigma), 50 mM tris.HCl (pH 9.5), 10 mM MgCl$_2$, 5 mM DTT and 2 units of T$_4$ polynucleotide kinase (P&L Biochemicals), for 30 min. at 37° C. The reaction is stopped by freezing at −80° C.

The radioactively labelled linker is then treated with 1 μg of ClaI and phosphatase and ligated with pHRi145 DNA (see above) in a 20 μl reaction volume containing 0.5 mM rATP (Sigma), 10 mM DTT (Calbiochem), 20 mM tris.HCl (pH 7.8), 1 mM MgCl$_2$ and 800 units of T$_4$ DNA ligase (Biolabs). The incubation is effected at 15° C. for 2 hours. The ligase is deactivated by incubation at 85° C. for 10 min. Subsequently, 2 volumes of water are added, the sodium chloride concentration is adjusted to 10 mM and 20 units of KpnI (Biolabs) are added over a period of 30 min at 37° C. After extraction with phenol and chloroform, the mixture is fractionated through a 0.9% low-melting agarose gel (Biorad) in 40 mM tris-.acetate (pH 7.8), 1 mM EDTA and 0.5 μg/ml ethidium bromide. The band visible by UV-irradiation which exhibits the same mobility as a marker DNA of the same size is cut out with a scalpel. The piece of gel is melted for 5 min. at 65° C. and then cooled to 37° C. A volume of approximately 20 μl is obtained. 5 μl of this solution are taken and incubated with 400 units of T$_4$ ligase (Biolabs) in 10 μl reaction volume, which is standardised against 0.5 mM ATP, 10 mM DTT, 10 mM MgCl$_2$, 20 mM tris.HCl (pH 7.8), for 12 hours at 15° C. 1/10 of the volume of a solution containing 100 mM tris.HCl (pH 7.5), 100 mM CaCl$_2$ and 100 mM MgCl$_2$ is added to the ligase mixture (solidified at 15° C.) and incubated at 65° C. for 5 min. The solution is then used to transform, as described above, *E. coli* HB101 cells that have been treated with calcium. Plating out is effected on McConkey agar plates supplemented by 50 μg/ml ampicillin.

The plasmid DNAs of 10 different colonies are isolated, as described above, and the DNA is subjected to the following restriction enzyme analysis: 0.5 μg in each case of plasmid DNA is cleaved in succession with KpnI (Biolabs), NcoI (Biolabs) and EcoRI (Biolabs) according to the directions of the enzyme manufacturer. The cleavage products are fractioned on 1% agarose gels in 40 mM tris.acetate (pH 7.8), 1 mM EDTA, 0.5 μg/ml ethidium bromide. All of the plasmids each exhibits one of these enzyme cleavage sites, as desired. One is designated HRi148.

The plasmid HRi148 contains a tryptophan-promotorooperator and a ribosomal binding site up to and including ATG and is an expression plasmid having a wide range of application.

Stage 2.15:

5 μg of plasmid DNA of pHRi148 are digested with the restriction endonucleases EcoRI and BamHI. Having been cut out, the vector pHRi148/EcoRI/BamHI is isolated by means of density gradient centrifugation.

The manufacture of the linearised vector obtained is also described in "Hans Rink et al., Nucleic Acids Research 12, 6369–6387 (1984)" in which the plasmid referred to in the present Application as pHRi148 is called pHR 148.

Stage 2.16:

20 μg of the DNA sequence F$_o$ obtained in accordance with Stage 2.11 are digested, in 20 μl of a solution of 50 μl of 100 mM tris.HCl (pH 7.5), 50 mM NaCl and 100 μg/ml gelatine, in succession with the restriction enzymes EcoRI and BamHI. The solution is standardised against TNE, whereupon 30 μg (=50 nmol of ends) of the vector DNA pHRi148/EcoRI/BamHI are added. The solution is extracted with phenol/-chloroform and the DNA is precipitated with alcohol. The DNA precipitate is treated in 20 μl of a solution of 50 mM tris.HCl (pH 7.8), 10 mM MgCl$_2$, 10 mM DTT, 0.5 mM ATP and 100 μg/ml gelatine with 25 units/μl T$_4$ DNA ligase (Biolabs) at 150° for 3 hours. In this manner, a recombined plasmid (pML1050) is formed in the solution.

Stage 2.17:

The transformation of *E. coli* HB101 with the plasmid pML1050 obtained in accordance with Stage 2.16 is carried out in the following manner:

The *E. coli* HB101 cells pretreated with calcium which are required for the transformation are manufactured as described by Mandel et al., J. Mol. Biol. 53, 159 (1970).

The solution obtained in accordance with Stage 2.16 which contains the recombined plasmid pML1050 is heated for 10 min. at 65° in order to deactivate the T4 DNA ligase and is then cooled to 37°. 10 μl of this reaction mixture are added to 150 μl of calcium-treated *E. coli* HB101 cells in 10 mM MgCl$_2$ and 10 mM tris.HCl (pH 7.5) in a total volume of 200 μl.

This mixture is then cooled in ice for 30 min., heated for 2 min. at 42° C. and then left to stand for 50 min. in 1 ml of L medium (cf. beginning of Example 2) at 37° C. The mixture is then applied in aliquots of 0.2 ml to 5 agar plates (McConkey agar, Difco) containing 60 μg/ml ampicillin (Serva). The agar plates are afterwards maintained at 37° C. for 16–18 hours. 109 ampicillin-resistant colonies of the transformed *E. coli* HB101 are obtained.

Stage 2.18:

30 of the transformed colonies obtained in accordance with Stage 2.17 are examined for their content of a fragment of the DNA sequence $F_o$ according to Stage 2.11 in the following manner:

The transformed colonies are pressed off onto nitrocellulose filters B85 (Schleicher and Schüll). In accordance with Grunstein and Hogness [Proc. Natl. Acad. Sci. USA 72, 3961 (1979)], the colonies are lysed and their denatured DNA is fixed to the filter. Prehybridisation of the filters is then carried out in 20 ml (per filter) of 4×SET [=solution of 30 mM tris.HCl (pH 8), 150 mM NaCl, 1 mM EDTA], 0.1% (w/v) Ficoll 400 (Pharmacia), 0.5% SDS, 50 μg/ml denatured calf's thymus DNA for 4 hours at 64° C. The nitrocellulose filters are then treated in 20 ml (per filter) of 5×SET (w/v) Ficoll 400, 0.2% SDS and 50 μg/ml denatured calf's thymus DNA for 16 hours at 64° C. with the $^{32}$P-radioactively marked probe (approx. 10$^3$–10$^4$ Cerencov cpm per filter). The oligodeoxynucleotide 64/73 (cf. Stage 2.10) is used as the probe.

Subsequently, the filters are washed twice in 2×SET, 0.2% SDS at room temperature, then twice in 2×SET, 0.5% SDS at 60° C. (first for 30 min, then for 60 min.). The filters are then dried between 3 MM paper (Whatman) and placed, at −80° C., on an X-ray film (Fuji) with an intensifying screen (Ilford) for 1–2 days.

The resulting autoradiograph shows 20 positive colonies (clones) which may be used for further processing, five of which are designated pML1050, pML1051, pML1052, pML1053 and pML1054.

Stage 2.19:

Characterisation of the inserted DNA sequence, i.e. the DNA insert, in the clone pML1050 obtained in accordance with Stage 2.18 is carried out in the following manner:

The DNA of the recombined plasmid pML1050 is isolated according to Ish-Horowitz (Molecular Cloning, A Laboratory Manual [published by T. Maniatis et al.], Cold Spring Harbor Lab. 1982, page 368). The nucleotide sequence of the $F_o$ DNA insert is determined according to Maxam and Gilbert [Proc. Natl. Acad. Sci. USA 74, 560 (1977); see also Meth. Enzym. 65, 499 (1980)]. For that purpose, 10 μg of plasmid DNA of pML1050 are cleaved with EcoRI and BamHI restriction endonucleases and the linearised DNAs are isolated by gel-elution from agarose gel. For that purpose, the linearised DNAs are purified by gel-electrophoresis over 1% low-melting agarose (Biorad) in tris-acetate-EDTA buffer pH 8. After colouring the DNA in the agarose gel with EtBr the area of the gel containing the DNA band is cut out of the gel and liquefied at 65° for 10 min. To this DNA solution are added 20 volumes of TNE, the DNA is purified according to Mueller et al. [J. Mol. Biol. 124, 343 (1978)] by DE-52 chromatography, extracted with phenol/chloroform and the DNA is precipitated with alcohol overnight at −20° C. The DNA precipitate is dissolved in 50 μl of 0.01M tris.HCl (pH 8), 0.1 mM EDTA and stored at −20° C. until use. Subsequently, the isolated DNAs are digested with alkaline phosphatase and chromatographed over DE-52. The DNAs are then radioactively labelled at the 5'-end with [γ-$^{32}$P]ATP (specific activity >5000 Ci/mmol, Amersham) and T4 polynucleotide kinase (P-L-Biochemicals).

The radioactively labelled DNAs are then cleaved with a second restriction endonuclease, for example PvuII and PstI. The resulting DNA fragments are isolated by gel-elution from agarose. Then, from the PvuII-EcoRI* fragment and PstI-BamHI* fragment the nucleotide sequence of the $F_o$ DNA is determined. (*indicates the radioactively labelled DNA end.)

EXAMPLE 3

Test-kit with monoclonal anti-CGRP II antibodies for determining CGRP IIa, competitive radioimmunoassay a. Manufacture of the monoclonal anti-CGRP antibodies (A) Immunisation of mice Pure CGRP II (3 mg) (manufactured in accordance with Example 1) in lyophilised form is dissolved in a small amount of 0.1% acetic acid and then made up to 3 ml with phosphate-buffered sodium chloride solution. The pH is adjusted to 7.2. Portions of this antigen solution are mixed with the same amounts of complete Freund's adjuvant or phosphate-buffered saline solution.

Female Balb/c mice (8 weeks old, obtained from the Tierfarm Sisseln, Switzerland) are injected intravenously with 100 μg of CGRP II solution in buffered saline solution. Four days later, the spleen is removed for fusion.

(B) Manufacture of the hybridoma and antibody test

The hybridoma cells are manufactured by fusing the spleen cells obtained with the myeloma cell line X63-Ag8.6.5.3 [J. F. Kearney et al., J. Immunol. 123, 1548 (1979)]. 10$^8$ spleen cells and 10$^7$ myeloma cells are used for this. The fusion is carried out as described [S. Alkan et al., Mol. Immunol. 20, 203 (1983)].

Determination of the anti-CGRP II activity in the hybridoma supernatants is carried out by means of a radioimmunoassay [RIA, T. Chard, An Introduction to Radioimmunoassay and related Techniques, North Holland Publ. Comp., Amsterdam 1978].

(C) Isolation and purification of the anti-CGRP II antibodies from ascitic fluid Balb/c mice are pretreated intraperitoneally with 0.4 ml of pristane (Carl Roth). After one week, from 2 to $5 \times 10^6$ cloned hybridoma cells are injected intraperitoneally. Ascitic fluid is taken repeatedly from each mouse and frozen at $-80°$ C. The collected fluid is thawed and centrifuged for 30 min. at 4° and 16,000 rev/min. The fat is filtered off with suction, and 0.9 volume equivalents of a saturated ammonium sulphate solution are slowly added dropwise, while stirring at 0°, to the remaining debris-free supernatant. The resulting crude immunoglobulin fraction is passed, using 0.1M tris.HCl (pH 8.2), through Sephacryl G 2000 (Pharmacia) as directed by the manufacturer. Active fractions are combined and concentrated with an Amicon XM50 filter (Amicon).

b. Test-kit for competitive radioimmunoassay

A solution of anti-CGRP II antibodies manufactured according to Example 3a(C) is diluted with phosphate-buffered saline solution (PBS solution) to a concentration of 1 μg per 100 μl. 100 μl of this solution are incubated for 2 hours at 37° C. in small plastics tubes or on plastics microtitre plates, antibodies being adsorbed non-specifically onto the plastics surface. In order to saturate the active sites still free on the plastics surface, after-treatment is carried out with a bovine serum albumin solution (BSA solution).

Dilution series of a sample solution or of the standard solution in BSA solution each have added to them 50 μl of a solution of CGRP II, labelled in known manner (29) with radioactive $^{125}$iodine, having an activity of 10,000 cpm per 50 μl and are then incubated on the plastics surface for 2 hours at 37° C. and then for 12 hours at 4° C. The small tubes or microtitre plates are washed with phosphate-buffered saline solution and the radioactivity is measured. The concentration of CGRP II in the sample solution is determined by a calibration curve generated with standard solution.

A test-kit for the described radioimmunoassay contains:
2 ml of solution of anti-CGRP II antibodies from Example 3a(C) having a concentration of from 1 to 10 mg per ml,
100 ml of phosphate-buffered saline solution (PBS solution),
100 ml of 0.3% bovine serum albumin and 0.1% sodium azide in PBS solution (BSA solution),
2 ml of solution of radioactive CGRP II having an activity of 200,000 cpm/ml,
2 ml of standard solution containing 100 ng/ml hirudine,
1 ml small tubes or microtitre plates of plastics material.

EXAMPLE 4

Gelatine solution

A sterile-filtered aqueous solution of CGRP II is mixed under aseptic conditions, while heating, with a sterile gelatine solution containing phenol as preservative, so that 1.0 ml of solution has the following composition:

| | |
|---|---|
| CGRP II | 10.0 μg |
| gelatine | 150.0 mg |
| phenol | 4.7 mg. |
| distilled water up to | 1.0 ml. |

The mixture is introduced into 1.0 ml phials under aseptic conditions.

EXAMPLE 5

Sterile dry substance for injection

5 μg of CGRP II are dissolved in 1 ml of an aqueous solution containing 20 mg of mannitol. The solution is sterile-filtered and, under aseptic conditions, introduced into a 2 ml ampoule, deep-frozen and lyophilised. Before being used, the lyophilisate is dissolved in 1 ml of distilled water or 1 ml of physiological saline solution. The solution is administered intramuscularly or intravenously. This formulation can also be introduced into double-chamber syringe ampoules.

EXAMPLE 6

Nasal Spray

200 μg of finely ground ($<5.0\mu$) CGRP II are suspended in a mixture of 3.5 ml of "Miglyol 812" and 0.08 g of benzyl alcohol. This suspension is introduced into a container having a metering valve. 5.0 ml of "Freon 12" are then introduced under pressure into the container through the valve. The "Freon" is dissolved in the Miglyol/benzyl alcohol mixture by shaking.

EXAMPLE 7

A solution of 2 ml of 0.6M ammonium acetate/0.1M KCl/1 mM EDTA is adjusted to pH 8 with concentrated ammonia solution and mixed with 100 μl of aqueous 1M CGRP IIa solution (cf. Example 2). 0.7 mg of carboxypeptidase Y (Carlsberg Biotechnology Ltd., Copenhagen, Denmark) is then added. After 30 min. at 25° C. the whole is acidified to pH 1 with 6M HCl. The reaction product is purified and isolated by means of HPLC under the conditions specified in Stage 1.7. CGRP II of the formula III is obtained which is identical to the product obtained in accordance with Example 1.

EXAMPLE 8

Analogously to Example 2, there is obtained by cultivating *Escherichia coli* clones that contain plasmids having the DNA sequence according to the formula XVII

```
MetAlaCysAsnThrAlaThrCysValThrHisArgLeuAlaGlyLeuLeuSer                    (XVII)
d(GAATTCATGGCTTGCAACACCGCTACCTGCGTTACCCACCGTCTGGCTGGTCTGCTGTCT
d(CTTAAGTACCGAACGTTGTGGCGATGGACGCAATGGGTGGCAGACCGACCAGACGACAGA
ArgSerGlyGlyMetValLysSerAsnPheValProThrAsnValGlySerLysAlaPhe
CGTTCTGGTGGTATGGTTAAATCTAACTTCGTTCCGACCAACGTTGGTTCTAAAGCTTTC
GCAAGACCACCATACCAATTTAGATTGAAGCAAGGCTGGTTGCAACCAAGATTTCGAAAG
GlyNON
GGTTAGGATCC)
```

CCAATCCTAGG)

and by analogous working up, CGRP IIb of the formula XIX.

fractions are concentrated by evaporation. The trifluoroacetic acid is removed as above by ion-exchange and

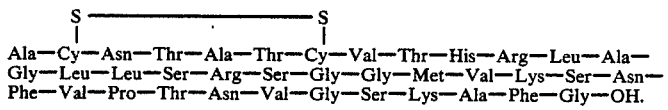

(XIX)

The starting materials are obtained analogously to Example 2.

EXAMPLE 9

4 mg of CGRP IIb (see Example 8) are incubated at 37° C. in 1 ml of 20 mM NaCl and 5 mM sodium phosphate at pH 7 for 20 hours with an amidation enzyme, isolated from 100 g of pig's hypophysis, as described in A. F. Bradbury, M. D. A. Finnie and D. G. Smyth, Nature 298, 686–688 (1982). Subsequently, acidification is carried out with 100 μl of 1M HCl. The reaction product is purified and isolated by means of HPLC under the conditions specified in Stage 1.7. CGRP II of the formula III is obtained which is identical to the product obtained in accordance with Example 1.

EXAMPLE 10

The peptide-amide, obtained in Stage 10.2, of the formula

CGRP II of the formula III is obtained by lyophilisation; retention time in the above analytical HPLC: 24 minutes, FAB/MS: MH+ 3794 (calculated molecular weight: 3793.4), $R_f$ (silica gel)=0.57 (n-butanol/pyridine/glacial acetic acid/water 35:35:7:23), $R_f$ (cellulose)=0.64 (n-butanol/pyridine/glacial acetic acid/water 38:24:8:30), $R_f$ (cellulose)=0.55 (n-butanol/pyridine/conc. ammonia/water 42:24:4:30).

The starting material is obtained in the following manner:

Stage 10.1: The peptide resin obtained in accordance with Example 1, Stage 1.4 is treated as follows in order to remove the protected peptide from the resin and in order to amidate the terminal carboxy group:

325 mg of peptide resin and 10 ml of dimethylformamide are placed in an autoclave, at −70° 6 g of ammonia are condensed in and the whole is left to react for 20 hours at room temperature. After distilling off the ammonia, 50 ml of diethyl ether are added to the remaining

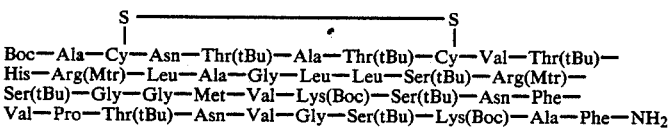

is dissolved in 2.8 ml of trifluoroacetic acid/water (9:1) and, after 1½ hours at room temperature, precipitated with 30 ml of cold diethyl ether and filtered off with suction. The filtration residue is dissolved in 5.2 ml of trifluoroacetic acid/water (95:5), left for 50 min. at 50°, cooled to room temperature and, after the addition of 60 μl of 1M ammonium iodide, left for 10 minutes at room temperature. By adding dropwise to 30 ml of cold diethyl ether the peptide-amide is precipitated. Having been filtered off with suction and dried, the peptideamide is dissolved in 3 ml of 0.1M acetic acid and traces of iodine still present are reduced by the addition of 15 μl of 1M sodium thiosulphate. The resulting solution is filtered through an ion-exchanger column (Amberlite ® IRA 93, acetate form 1.2×8 cm) and eluted with 0.1M acetic acid. After concentrating to dryness by evaporation, the residue is dissolved in 3 ml of bidistilled water, left overnight under argon at room temperature and this solution is used for preparative HPLC purification; conditions: column: Vydac 5 μm C18, 250×10 mm (The Separations Group, Hesperia, California, USA), gradient, consisting of the solutions A (0.1% by volume trifluoroacetic acid in water) and 25%–30% by volume B (0.1% by volume trifluoroacetic acid in acetonitrile) in 30 minutes and also A and 30%–40% by volume B in 5 minutes; flow rate: 4 ml/minute; detection: 210 nm. The main peak is collected in fractions and the purity thereof is determined by analytical HPLC; conditions: column: Vydac 5 μm C18, 250×4.6 mm; gradient consisting of A and B: 20%–45% B in 45 minutes; A and B as above. The pure suspension. After 2 hours at 0°, the precipitate is filtered off with suction. The protected peptide-amide is extracted from the resin with glacial acetic acid (five times with 5 ml), the acetic acid is removed by lyophilisation and the residue is suspended in 20 ml of methanol/water (9:1). When the protected peptide-amide has been centrifuged off, washed and dried 77 mg thereof are obtained.

Stage 10.2: For conversion into the disulphide, a solution of 69 mg of the product obtained in accordance with Stage 10.1 in 14 ml of glacial acetic acid/water (4:1) is added dropwise in 4 minutes while stirring at room temperature to a solution of 164 mg of iodine in 34 ml of glacial acetic acid and 16 ml of water. After a further 10 minutes, the reaction is terminated by the addition of 1.4 ml of 1M sodium acetate and 0.68 ml of 1M ascorbic acid. The salts are separated off over a Biogel P2 column (2.5×34 cm, in glacial acetic acid/water [6:4]). After being concentrated, the peptide-containing fraction is lyophilised, the residue is suspended in 5 ml of methanol and the insoluble, protected peptide-amide is obtained by centrifugation and drying.

EXAMPLE 11

1 g of H-Ala-Cys(MOB)-Asn(XANT)-Thr(BZL)-Ala-Thr(BZL)-Cys(MOB)-Val-Thr(BZL)-His(TOS)-Arg(TOS)-Leu-Ala-Gly-Leu-Leu-Ser(BZL)-Arg(TOS)-Ser(BZL)-Gly-Gly-Met-Val-Lys(2CZ)-Ser(BZL)-Asn(XANT)-Phe-Val-Pro-Thr(BZL)-

Asn(XANT)-Val-Gly-Ser(BZL)-Lys(2CZ)-Ala-Phe-MBHA resin and 1 ml of anisole are stirred in a Teflon apparatus for 1 hour at 0° with 10 ml of dry HF. After distilling off the HF and drying under a high vacuum, the residue is extracted five times with 10 ml of diethyl ether. The peptide is extracted from the resin with degassed 0.1N acetic acid, diluted to 500 ml with degassed water, and the pH is adjusted to 8.4 with ammonia. After stirring overnight at room temperature, no free mercapto groups can be detected. The solution is highly concentrated and lyophilised, and the residue is purified by preparative HPLC, as described in Example 10. The resulting fractions are tested for their purity in a thin-layer chromatogram in the system n-butanol/pyridine/glacial acetic acid/water (35:35:7:23) over silica gel ($R_f$=0.57) and, if necessary, again purified by HPLC. The combined pure fractions are concentrated by evaporation in vacuo and the residue is lyophilised from water. CGRP II of the formula III is obtained; $R_f$(cellulose)=0.64 (n-butanol/pyridine/glacial acetic acid/water 38:24:8:30).

The starting material is obtained as follows:

Stage 11.1: 1 g of MBHA-polystyrene hydrochloride (polystyrene resin crosslinked with divinylbenzene in which some phenyl groups carry an amino-(4-methyl-phenyl)-methyl substituent; supplier: Applied Biosystems, 850 Lincoln Centre Dr., Foster City, CA 94404, USA; charge 0.57 mmol/g) is treated in the machine described in Example 1, Stage 1.3, as follows (approximately 20 ml in each case):

3×0.5 min. dimethylacetamide, degassed,
3×2 min. 10% diisopropylethylamine in dimethylacetamide,
6×0.5 min. dimethylacetamide, distilled,
1×120 min. coupling: 455 mg (1.7 mmol) of Boc-Phe, 230 mg of hydroxybenzotriazole, 385 mg of dicyclohexylcarbodiimide in 0.36 ml of ethylene chloride and 4 ml of dimethyl acetamide: 120 min. at room temperature,
1×5 min. 10 ml of acetic anhydride/pyridine/dimethylacetamide (10:10:80),
1×0.5 min. dimethylacetamide, degassed,
1×1 min. isopropanol,
2×0.5 min. ethylene chloride, 2×0.5 min. dimethylacetamide,
1×1 min. isopropanol, 3×0.5 min. ethylene chloride/ethanedithiol (99:1),
2×5 min., 1×15 minutes trifluoroacetic acid/ethylene chloride/ethanedithiol (50:49:1) to remove the Boc group, 3×0.5 min. ethylene chloride/ethanedithiol (99:1).

The cycle then recommences from the beginning.

The following amino acids are condensed on in succession:

Boc-Ala, Boc-Lys(2CZ), Boc-Ser(BZL), Boc-Gly, Boc-Val, Boc-Asn(XANT), Boc-Thr(BZL), Boc-Pro, Boc-Val, Boc-Phe, Boc-Asn(XANT), Boc-Ser(BZL), Boc-Lys(2CZ), Boc-Val, Boc-Met, Boc-Gly, Boc-Gly, Boc-Ser(BZL), Boc-Arg(TOS), Boc-Ser(BZL), Boc-Leu, Boc-Leu, Boc-Gly, Boc-Ala, Boc-Leu, Boc-Arg(TOS), Boc-His(TOS), Boc-Thr(BZL), Boc-Val, Boc-Cys(MOB), Boc-Thr(BZL), Boc-Ala, Boc-Thr(BZL), Boc-Asn(XANT), Boc-Lys(MOB) and Boc-Ala. The completeness of the coupling reaction is tested qualitatively using the Kaiser test. If the test is positive, the coupling is repeated. After removing the Boc group from the last alanine, the resin is dried under a HV.

We claim:

1. A peptide fragment of human calcifonin gene related peptide of at least 37 amino acids up to 90 amino acids containing at least the 37 amino acid sequence of the formula —Ala—Cys—Asn—Thr—Ala—Thr—Cys—Val—Thr—His—

—Arg—Leu—Ala—Gly—Leu—Leu—Ser—Arg—Ser—Gly—

—Gly—Met—Val—Lys—Ser—Asn—Phe—Val—Pro—Thr—

—Asn—Val—Gly—Ser—Lys—Ala—Phe— the Cys resides within said 37 amino acid sequence being free or forming an intra- or inter-molecular disulfide bridge, said peptide being a fragment of human calcitonin gene related peptide; the carboxy terminus of said fragment being a free carboxy group or amidated by NH$_2$; the amino terminus of said fragment being a free amino group or acetylated; or a pharmaceutically acceptable salt thereof.

2. The peptide; amidated, acetylated, or amidated and acetylated peptide; or pharmaceutically acceptable salt thereof of claim 1 having up to 72 amino acids.

3. A pharmaceutically acceptable salt of a compound according to claim 1.

4. The amidated peptide of claim 2 of the formula

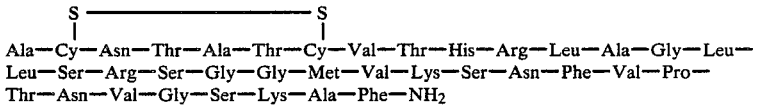

or a pharmaceutically acceptable salt thereof.

5. The peptide of the formula

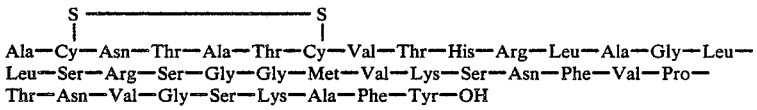

or a pharmaceutically acceptable salt thereof.

6. The peptide of the formula

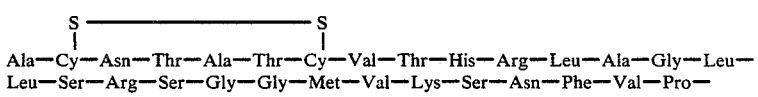

Thr—Asn—Val—Gly—Ser—Lys—Ala—Phe—Gly—OH or a pharmaceutically acceptable salt thereof.

7. A composition of matter comprising at least 50% of a compound of claim 4 or a pharmaceutically acceptable salt thereof.

8. A pharmaceutical preparation for the treatment of a coronary circulation disorder comprising (a) a therapeutically effective amount of aN amidated peptide of claim 2 or a pharmaceutically acceptable salt thereof; together with (b) more than 95% by weight of a pharmaceutically acceptable carrier.

9. A method of treating a coronary circulation disorder in a human in need thereof comprising administering to said human a therapeutically effective amount of the amidated peptide of claim 4 or a pharmaceutically acceptable salt thereof.

* * * * *